(12) United States Patent
Dehmlow et al.

(10) Patent No.: US 8,748,434 B2
(45) Date of Patent: Jun. 10, 2014

(54) 1,2-PYRIDAZINES, 1,6-PYRIDAZINES AND PYRIMIDINES

(71) Applicant: Hoffman-La Roche Inc., Nutley, NJ (US)

(72) Inventors: Henrietta Dehmlow, Loerrach (DE); Shawn David Erickson, Leonia, NJ (US); Patrizio Mattei, Riehen (CH); Hans Richter, Grenzach-Wyhlen (DE)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 13/856,057

(22) Filed: Apr. 3, 2013

(65) Prior Publication Data

US 2013/0267519 A1    Oct. 10, 2013

(30) Foreign Application Priority Data

Apr. 4, 2012 (EP) .................................. 12163089

(51) Int. Cl.
*C07D 237/00* (2006.01)
*C07D 239/00* (2006.01)
*A01N 43/54* (2006.01)
*A01N 43/58* (2006.01)
*A01N 43/40* (2006.01)

(52) U.S. Cl.
USPC ........... 514/256; 514/247; 514/277; 544/224; 544/242

(58) Field of Classification Search
None
See application file for complete search history.

(56) References Cited

FOREIGN PATENT DOCUMENTS

WO    2012/117000 A1    9/2012

OTHER PUBLICATIONS

Hillers et al. Analogs of purine nucleosides and purinemono- and polynucleotides. V. Preparation of 9-(1,5-dihydroxy-3-pentyl)purines. Khimiya Geterotsiklicheskikh Soedinenii (1976), (4), 552-5.*

Gillers et al. Analogs of purine nucleosides and purinemono- and polynucleotides. V. Preparation of 9-(1,5-dihydroxy-3-pentyl)purines. Khimiya Geterotsiklicheskikh Soedinenii (1976), (4), 431-434.*

* cited by examiner

*Primary Examiner* — Jeffrey H Murray
*Assistant Examiner* — Oluwafemi Masha
(74) *Attorney, Agent, or Firm* — Robert C. Hall

(57) ABSTRACT

This invention relates to novel 1,2-pyridazines, 1,6-pyridazines or pyrimidines of the formula wherein $B^1$ to $B^3$ and $R^1$ to $R^7$ are as defined in the description and in the claims, as well as pharmaceutically acceptable salts thereof. These compounds are GPBAR1 agonists and may therefore be useful as medicaments for the treatment of diseases such as type II diabetes.

15 Claims, No Drawings

1,2-PYRIDAZINES, 1,6-PYRIDAZINES AND PYRIMIDINES

CROSS REFERENCE TO RELATED APPLICATIONS

This Application claims priority under 35 USC §119 to EP Application No. 12163089.1 filed on Apr. 4, 2012, the disclosure of which is incorporated herein by reference.

FIELD OF THE INVENTION

The present invention relates to novel 1,2-pyridazines, 1,6-pyridazines or pyrimidines having pharmaceutical activity, their manufacture, pharmaceutical compositions containing them and their potential use as medicaments.

BACKGROUND OF THE INVENTION

Diabetes mellitus is an ever-increasing threat to human health. For example, in the United States current estimates maintain that about 16 million people suffer from diabetes mellitus. Type II diabetes also known as non-insulin-dependent diabetes mellitus accounts for approximately 90-95% of diabetes cases, killing about 193,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary lifestyle, diet, and obesity now prevalent in developed countries. About 80% of diabetics with type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature on set, can develop at any age, but most commonly becomes apparent during adulthood. However, the incidence of type II diabetes in children is rising. In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulfonylureas, which increase insulin production from pancreatic β-cells; glucose-lowering effectors, such as metformin which reduce glucose production from the liver; activators of the peroxisome proliferator-activated receptor γ (PPARγ), such as the thiazolidinediones, which enhances insulin action; and α-glucosidase inhibitors which interfere with gut glucose production. There are, however, deficiencies associated with currently available treatments. For example sulfonylureas and insulin injections can be associated with hypoglycemic episodes and weight gain. Furthermore, patients often lose responsiveness to sulfonylureas over time. Metformin and α-glucosidase inhibitors often lead to gastrointestinal problems and PPARγ agonists tend to cause increased weight gain and edema.

Bile acids (BA) are amphipathic molecules which are synthesized in the liver from cholesterol and stored in the gall bladder until secretion to the duodenum and intestine to play an important role in the solubilization and absorption of dietary fat and lipid-soluble vitamins. Approx. 99% of BA are absorbed again by passive diffusion and active transport in the terminal ileum and transported back to the liver via the portal vein (enterohepatic circulation). In the liver, BA decrease their own biosynthesis from cholesterol through the activation of the farnesoid X receptor alpha (FXRα) and small heterodimer partner (SHP), leading to the transcriptional repression of cholesterol 7α-hydroxylase, the rate-limiting step of BA biosynthesis from cholesterol.

GPBAR1, in the literature termed TGR5, M-BAR or BG37 as well, was recently identified as a G-protein coupled receptor (GPCR) responsive to BA (Kawamata et al., *J. Biol. Chem.* 2003, 278, 9435-9440; Maruyama et al., *Biochem. Biophys. Res. Commun.* 2002, 298, 714-719). GPBAR1 is a G(alpha)s-coupled GPCR and stimulation by ligand binding causes activation of adenylyl cyclase which leads to the elevation of intracellular cAMP and subsequent activation of downstream signaling pathways. The human receptor shares 86, 90, 82, and 83% amino acid identity to bovine, rabbit, rat, and mouse receptor, respectively. GPBAR1 is abundantly expressed in the intestinal tract, monocytes and macrophages, lung, spleen, placenta (Kawamata et al., *J. Biol. Chem.* 2003, 278, 9435-9440). BA induced receptor internalization, intracellular cAMP production and activation of extracellular signal-regulated kinase in GPBAR1-expressing HEK293 and CHO cells.

GPBAR1 was found to be abundantly expressed in monocytes/macrophages from humans and rabbits (Kawamata et al., *J. Biol. Chem.* 2003, 278, 9435-9440), and BA treatment suppressed LPS-induced cytokine production in rabbit alveolar macrophages and human THP-1 cells expressing GPBAR1. These data suggest that bile acids can suppress the macrophage function via activation of GPBAR1. In the liver functional GPBAR1 was found in the plasma membranes of Kupffer cells, mediating inhibition of LPS-induced cytokine expression (Keitel, *Biochem. Biophys. Res. Commun.* 2008, 372, 78-84), and of sinusoidal endothelial cells, where bile salts led to an increase in intracellular cAMP and to the activation and enhanced expression of the endothelial nitric oxide (NO) synthase (Keitel, *Hepatology* 2007, 45, 695-704). Furthermore, GPBAR1 has been detected in cholangiocytes of rat liver (Keitel, *Biochem. Biophys. Res. Commun.* 2008, 372, 78-84). Hydrophobic bile acids, such as taurolithocholic acid, increase cAMP in cholangiocytes suggesting that GPBAR1 may modulate ductal secretion and bile flow. Indeed, GPBAR1 staining colocalized with the cyclic adenosine monophosphate regulated chloride channel cystic fibrosis transmembrane conductance regulator (CFTR) and the apical sodium-dependent bile salt uptake transporter (ASBT). A functional coupling of GPBAR1 to chloride secretion and bile flow has been shown using GPBAR1 agonists (Keitel et al., *Hepatology* 2009 50, 861-870; Pellicciari et al.,

*J Med Chem* 2009, 52(24), 7958-7961). In summary, GPBAR1 agonists may trigger a protective as well as medicative mechanism in cholestatic livers.

GPBAR1 is expressed in intestinal enteroendocrine cell lines from human (NCI-H716) and murine (STC-1, GLUTag) origin (Maruyama et al., *Biochem. Biophys. Res. Commun.* 2002, 298, 714-719). Stimulation of GPBAR1 by BA stimulated cAMP production in NCI-H716 cells. Intracellular increases in cAMP suggested that BA may induce the secretion of glucagon-like peptide-1 (GLP-1). Indeed, activation of GPBAR1 by BA promoted GLP-1 secretion in STC-1 cells (Katsuma et al., *Biochem. Biophys. Res. Commun.* 2005, 329, 386-390). Receptor-specificity has been demonstrated by RNA interference experiments which revealed that reduced expression of GPBAR1 resulted in diminished secretion of GLP-1. There is compelling evidence that GPBAR1-mediated GLP-1 and PYY release from intestinal L-cells extends to in vivo. In the isolated vascularly perfused rat colon, BAs have been shown to trigger GLP-1 secretion (Plaisancie et al., *J. Endocrin.* 1995, 145, 521-526). Using a combination of pharmacological and genetic gain- and loss-of-function studies in vivo, GPBAR1 signaling was shown to induce GLP-1 release, leading to improved liver and pancreatic function and enhanced glucose tolerance in obese mice (Thomas et al., *Cell Metabolism,* 2009, 10, 167-177). In humans, intracolonic administration of deoxycholate showed marked increases in plasma levels of GLP-1 and the co-secreted PYY (Adrian et al., *Gut* 1993, 34, 1219-1224).

GLP-1 is a peptide secreted from enteroendocrine L cells has been shown to stimulate insulin release in glucose dependent manner in humans (Kreymann et al., *Lancet* 1987, 2, 1300-1304) and studies in experimental animals demonstrated that this incretin hormone is necessary for normal glucose homeostasis. In addition, GLP-1 can exert several beneficial effects in diabetes and obesity, including 1) increased glucose disposal, 2) suppression in glucose production, 3) reduced gastric emptying, 4) reduction in food intake and 5) weight loss. More recently, much research has been focused on the use of GLP-1 in the treatment of conditions and disorders such as diabetes mellitus, stress, obesity, appetite control and satiety, Alzheimer disease, inflammation, and diseases of the central nervous system. (see, for example, Bojanowska et al., *Med. Sci. Monit.* 2005, 8, RA271-8; Perry et al., *Current Alzheimer Res.* 2005, 3, 377-385; and Meier et al., *Diabetes Metab. Res. Rev.* 2005, 2, 91-117). However, the use of a peptide in clinical treatment is limited due to difficult administration, and in vivo stability. Therefore, a small molecule that either mimics the effects of GLP-1 directly, or increases GLP-1 secretion, may be useful in treatment of the variety of conditions or disorders described above, namely diabetes mellitus.

PYY is co-secreted with GLP-1 from intestinal L-cells following a meal. An dipeptidyl peptidase-IV (DPP4) cleavage product of PYY is PYY[3-36] (Eberlein et al. *Peptides* 1989, 10, 797-803) (Grandt et al. *Regul Pept* 1994, 51, 151-159). This fragment constitutes approximately 40% of total PYY-like immunoreactivity in human and canine intestinal extracts and about 36% of total plasma PYY immunoreactivity in a fasting state to slightly over 50% following a meal. PYY[3-36] is reportedly a selective ligand at the Y2 and Y5 receptors. Peripheral administration of PYY reportedly reduces gastric acid secretion, gastric motility, exocrine pancreatic secretion (Yoshinaga et al. *Am J Physiol* 1992, 263, G695-701), gallbladder contraction and intestinal motility (Savage et al. Gut 1987, 28, 166-170). It has been demonstrated that intra-arcuate (IC) or intra-peritoneal (IP) injection of PYY3-36 reduced feeding in rats and, as a chronic treatment, reduced body weight gain. Intra-venous (IV) infusion (0.8 pmol/kg/min) for 90 min of PYY3-36 reduced food intake in obese and normal human subjects 33% over 24 hours. These finding suggest that the PYY system may be a therapeutic target for the treatment of obesity (Bloom et. al. *Nature* 2002, 418, 650-654).

Furthermore, activation of GPBAR1 might be beneficial for the treatment of obesity and metabolic syndrome. Mice fed a high fat diet (HFD) containing 0.5% cholic acid gained less weight than control mice on HFD alone independent of food intake (Watanabe et al., *Nature* 2006, 439, 484-489). These effects were independent of FXR-alpha, and are likely to results from the binding of BA to GPBAR1. The proposed GPBAR1-mediated mechanism is leading to the subsequent induction of the cAMP-dependent thyroid hormone activating enzyme type 2 (D2) which converts the inactive T3 into the active T4, resulting in the stimulation of the thyroid hormone receptor and promoting energy expenditure. Mice lacking the D2 gene were resistant to cholic acid-induced weight loss. In both rodents and humans, the most thermogenically important tissues (the brown adipose and skeletal muscle) are specifically targeted by this mechanism because they co-express D2 and GPBAR1. The BA-GPBAR1-cAMP-D2 signalling pathway is therefore a crucial mechanism for fine-tuning energy homeostasis that can be targeted to improve metabolic control.

SUMMARY OF THE INVENTION

The present invention relates to 1,2-pyridazines, 1,6-pyridazines and pyrimidines of the formula

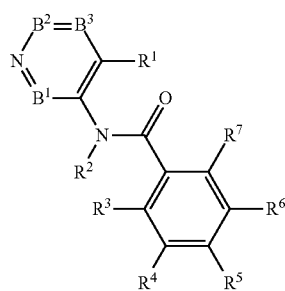

I wherein
$B^1$ is N and $B^2$ is $CR^9$ and $B^3$ is $CR^{10}$, or
$B^1$ is $CR^8$ and $B^2$ is N and $B^3$ is $CR^{10}$, or
$B^1$ is $CR^8$ and $B^2$ is $CR^9$ and $B^3$ is N;
$R^1$ is selected from the group consisting of
  phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkoxy, hydroxy-$C_{1-7}$-alkyl, hydroxy-$C_{1-7}$-alkoxy, $C_{1-7}$-alkoxy-$C_{1-7}$-alkyl, amino, $C_{1-7}$-alkylamino, di-$C_{1-7}$-alkylamino and phenyl-$C_{1-7}$-alkoxy, and
  heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy,
$R^2$ is selected from the group consisting of $C_{1-7}$-alkyl, halogen-$C_{1-7}$-alkyl, aminocarbonyl-$C_{1-7}$-alkyl and $C_{1-7}$-alkyl-sulfonyl-$C_{1-7}$-alkyl;

$R^3$ and $R^7$ are independently selected from the group consisting of hydrogen, halogen, $C_{1-7}$-alkyl and $C_{1-7}$-alkoxy;

$R^4$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$- alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxycarbonyl-$C_{1-7}$-alkylsulfonyl, heterocyclylsulfonyl, aminosulfonyl, $C_{1-7}$-alkylaminosulfonyl, di-$C_{1-7}$-alkyl-aminosulfonyl, amino, $C_{1-7}$-alkylamino, di-$C_{1-7}$-alkylamino, nitro, unsubstituted heterocyclyl or heterocyclyl substituted with one or two groups selected from halogen, oxo and $C_{1-7}$-alkyl;

$R^5$ is selected from the group consisting of hydrogen, $C_{1-7}$-alkyl, halogen, halogen-$C_{1-7}$-alkyl and $C_{1-7}$-alkoxy; and $R^8$, $R^9$ and $R^{10}$ are independently selected from the group consisting of hydrogen, $C_{1-7}$-alkyl, halogen and halogen-$C_{1-7}$-alkyl;

or pharmaceutically acceptable salts thereof.

The compounds are modulators or ligands of the GPBAR1 receptor. More particularly, the compounds are potent GPBAR1 agonists and may be useful for the treatment and prevention of metabolic and inflammatory diseases, in particular type II diabetes.

It is an object of the present invention to provide selective, directly acting GPBAR1 agonists. Such agonists are useful as therapeutically active substances, particularly in the treatment and/or prevention of diseases which are associated with the activation of GPBAR1.

The novel compounds of the present invention exceed the compounds known in the art, inasmuch as they are small molecules and they bind to and selectively activate GPBAR1 very efficiently. They are expected to have an enhanced therapeutic potential compared to the compounds already known in the art and can be used for the treatment of diabetes, obesity, metabolic syndrome, hypercholesterolemia, dyslipidemia and a wide range of acute and chronic inflammatory diseases.

The invention is also concerned with processes for the manufacture of compounds of formula I.

The invention also relates to pharmaceutical compositions comprising a compound of formula I as described above and a pharmaceutically acceptable carrier and/or adjuvant.

A further aspect of the invention is the use of compounds of formula I as therapeutic active substances for the treatment of diseases which are associated with the modulation of GPBAR1 activity. The invention thus relates to a method for the treatment of a disease associated with the modulation of GPBAR1 activity such as for example diabetes, particularly type II diabetes or gestational diabetes.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and stereoisomers, solvates or salts thereof (e.g., pharmaceutically acceptable salts).

The term "substituent" denotes an atom or a group of atoms replacing a hydrogen atom on the parent molecule.

The term "halogen" refers to fluoro, chloro, bromo and iodo, with fluoro, chloro and bromo being of particular interest. More particularly, halogen refers to fluoro and chloro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. The term "$C_{1-10}$-alkyl" refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. More particularly, the term "alkyl" also embraces lower alkyl groups as described below.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl.

The term "cycloalkyl" or "$C_{3-7}$-cycloalkyl" denotes a saturated moncyclic hydrocarbon group containing from 3 to 7 carbon atoms, such as cyclopropyl, cyclobutyl, cyclopentyl, cyclohexyl or cycloheptyl, more particularly cyclopropyl. In addition, the term "cycloalkyl" also embraces bicyclic hydrocarbon groups containing from 3 to 10 carbon atoms. Bicyclic means consisting of two saturated carbocycles having one or more carbon atoms in common. Examples for bicyclic cycloalkyl are bicyclo[2.2.1]heptanyl or bicyclo[2.2.2]octanyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower cycloalkylalkoxy" or "$C_{3-7}$-cycloalkyl-$C_{1-7}$-alkoxy" refers to lower alkoxy groups as defined above wherein at least one of the hydrogen atoms of the lower alkoxy group is replaced by a cycloalkyl group. Among the lower cycloalkylalkoxy groups of particular interest resides cyclopropylmethoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl and 2-methoxyethyl.

The term hydroxy means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower hydroxyalkoxy" or "hydroxy-$C_{1-7}$-alkoxy" refers to lower alkoxy groups as defined above wherein at least one of the hydrogen atoms of the lower alkoxy group is replaced by a hydroxyl group. Among the lower hydroxyalkoxy groups of particular interest are hydroxymethoxy or 2-hydroxyethoxy.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl being of more particular interest.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the lower halogenalkoxy groups of particular interest are trifluoromethoxy, difluoromethoxy, fluormethoxy and chloromethoxy, more particularly trifluoromethoxy.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxylalkyl groups or particular interest are carboxylmethyl (—$CH_2$—COOH) and carboxylethyl (—$CH_2$—$CH_2$—COOH).

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A particular lower alkoxycarbonylalkyl group is —$CH_2$—$COOCH_3$.

The term "lower alkylsulfonyl" or "$C_{1-7}$-alkylsulfonyl" means the group —$S(O)_2$—R, wherein R is a lower alkyl group as defined above. A lower alkylsulfonyl group of particular interest is methylsulfonyl.

The term "aminosulfonyl" means the group —$S(O)_2$—$NH_2$.

The term "lower alkylaminosulfonyl" or "$C_{1-7}$-alkylaminosulfonyl" defines the group —$S(O)_2$—NH—R, wherein R is lower alkyl and the term "lower alkyl" has the previously given meaning. An example of a lower alkylaminosulfonyl group is methylaminosulfonyl.

The term "di-lower alkylaminosulfonyl" or "di-$C_{1-7}$-alkylaminosulfonyl" defines the group —$S(O)_2$—NRR', wherein R and R' are lower alkyl groups as defined above. An example of a di-lower alkylaminosulfonyl group is dimethylaminosulfonyl.

The term "heterocyclylsulfonyl" defines a group —$S(O)_2$—Het, wherein Het is a heterocyclyl group as defined herein below.

"Amino" refers to the group —$NH_2$. The term "$C_{1-7}$-alkylamino" means a group —NHR, wherein R is lower alkyl and the term "lower alkyl" has the previously given significance. The term "di-$C_{1-7}$-alkylamino" means a group —NRR', wherein R and R' are lower alkyl groups as defined above.

The term "lower hydroxyalkylsulfonyl" or "hydroxy-$C_{1-7}$-alkylsulfonyl" refers to lower alkylsulfonyl groups as defined above wherein at least one of the hydrogen atoms of the lower alkylsulfonyl group is replaced by a hydroxy group. Among the particular interesting lower hydroxyalkylsulfonyl groups are hydroxyethylsulfonyl.

The term "lower alkoxycarbonylalkylsulfonyl" or "$C_{1-7}$-alkoxycarbonyl-$C_{1-7}$-alkylsulfonyl" refers to lower alkylsulfonyl groups as defined above wherein at least one of the hydrogen atoms of the lower alkylsulfonyl group is replaced by a lower alkoxycarbonyl group. Among the particular interesting lower alkoxycarbonyl-alkylsulfonyl groups is —$S(O)_2$—$(CH_2)_2$—$COOCH_3$.

The term "carboxylalkylsulfonyl" or "carboxyl-$C_{1-7}$-alkylsulfonyl" refers to lower alkylsulfonyl groups as defined above wherein at least one of the hydrogen atoms of the lower alkylsulfonyl group is replaced by a carboxyl group. Among the particular interesting lower carboxyl-alkylsulfonyl groups are —$S(O)_2$—$(CH_2)_3$—COOH or —$S(O)_2$—$(CH_2)_4$—COOH.

"Amino" refers to the group —$NH_2$. The term "$C_{1-7}$-alkylamino" means a group —NHR, wherein R is lower alkyl and the term "lower alkyl" has the previously given significance. The term "di-$C_{1-7}$-alkylamino" means a group —NRR', wherein R and R' are lower alkyl groups as defined above.

The term "cyano" refers to the group —CN. The term "lower cyanoalkoxy" or "cyano-$C_{1-7}$-alkoxy" refers to a lower alkoxy group as defined above wherein at least one of the hydrogen atoms of the lower alkoxy group is replaced by a cyano group.

The term "nitro" refers to the group —$NO_2$.

The term "lower phenylalkoxy" or "phenyl-$C_{1-7}$-alkoxy" means lower alkoxy groups as defined above wherein one of the hydrogen atoms of the lower alkoxy group is replaced by an optionally substituted phenyl group.

The term "heterocyclyl" refers to a saturated or partly unsaturated monocyclic or bicyclic ring containing from 3 to 10 ring atoms which can comprise one, two or three atoms selected from nitrogen, oxygen and/or sulfur. Bicyclic means consisting of two cycles having two ring atoms in common, i.e. the bridge separating the two rings is either a single bond or a chain of one or two ring atoms. Examples of monocyclic heterocyclyl rings containing in particular from 3 to 7 ring atoms include azirinyl, azetidinyl, oxetanyl, piperidinyl, piperazinyl, azepinyl, diazepanyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolidinyl, dihydrofuryl, tetrahydrofuryl, tetrahydropyranyl, tetrahydrothiopyranyl, 1,1-dioxo-hexahydro-1,6-thiopyranyl, thiomorpholinyl and 1,1-dioxo-1λ6-thiomorpholinyl. Examples of bicyclic heterocyclyl rings are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, or dihydropyranyl.

The term "heteroaryl" in general refers to an aromatic 5- or 6-membered ring which comprises one, two, three or four atoms selected from nitrogen, oxygen and/or sulfur, such as pyridyl, pyrazinyl, pyrimidinyl, 2,4-dioxo-1H-pyrimidinyl, pyridazinyl, 2-oxo-1,2-dihydropyridinyl, pyrrolyl, oxazolyl, oxadiazolyl, isoxazolyl, thiadiazolyl, tetrazolyl, pyrazolyl, imidazolyl, furanyl, thiazolyl, isothiazolyl, triazolyl, tetrazolyl, thienyl, azepinyl, diazepinyl. The term "heteroaryl" further refers to bicyclic aromatic groups comprising from 5 to 12 ring atoms, in which one or both rings can contain one, two or three atoms selected from nitrogen, oxygen or sulfur, such as quinolinyl, isoquinolinyl, cinnolinyl, quinazolinyl, pyrazolo[1,5-a]pyridyl, imidazo[1,2-a]pyridyl, quinoxalinyl, benzofuranyl, benzothienyl, benzothiazolyl, benzotriazolyl, indolyl and indazolyl. More particularly, "heteroaryl" refers to an aromatic 6-membered ring selected from the group consisting of pyridyl, pyrazinyl pyrimidinyl and pyridazinyl, more particularly pyridyl.

The term "oxo" means that a C-atom of the heterocyclyl or heteroaryl ring may be substituted by =O, thus meaning that the heterocyclyl or heteroaryl ring may contain one or more carbonyl (—CO—) groups.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

The term "modulator" denotes a molecule that interacts with a target. The interactions include e.g. agonistic, antagonistic, or inverse agonistic activity.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

In detail, the present invention relates to compounds of the formula

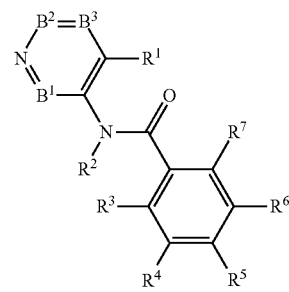

I wherein $B^1$ is N and $B^2$ is $CR^9$ and $B^3$ is $CR^{10}$, or $B^1$ is $CR^8$ and $B^2$ is N and $B^3$ is $CR^{10}$, or $B^1$ is $CR^8$ and $B^2$ is $CR^9$ and $B^3$ is N;

$R^1$ is selected from the group consisting of phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkoxy, hydroxy-$C_{1-7}$-alkyl, hydroxy-$C_{1-7}$-alkoxy, $C_{1-7}$-alkoxy-$C_{1-7}$-alkyl, amino, $C_{1-7}$-alkylamino, di-$C_{1-7}$-alkylamino and phenyl-$C_{1-7}$-alkoxy, and heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy, $R^2$ is selected from the group consisting of $C_{1-7}$-alkyl, halogen-$C_{1-7}$-alkyl, aminocarbonyl-$C_{1-7}$-alkyl and $C_{1-7}$-alkylsulfonyl-$C_{1-7}$-alkyl;

$R^3$ and $R^7$ are independently selected from the group consisting of hydrogen, halogen, $C_{1-7}$-alkyl and $C_{1-7}$-alkoxy;

$R^4$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxycarbonyl-$C_{1-7}$-alkylsulfonyl, heterocyclylsulfonyl, aminosulfonyl, $C_{1-7}$-alkylaminosulfonyl, di-$C_{1-7}$-alkyl-aminosulfonyl, amino, $C_{1-7}$-alkylamino, di-$C_{1-7}$-alkylamino, nitro, unsubstituted heterocyclyl or heterocyclyl substituted with one or two groups selected from halogen, oxo and $C_{1-7}$-alkyl;

$R^5$ is selected from the group consisting of hydrogen, $C_{1-7}$-alkyl, halogen, halogen-$C_{1-7}$-alkyl and $C_{1-7}$-alkoxy; and $R^8$, $R^9$ and $R^{10}$ are independently selected from the group consisting of hydrogen, $C_{1-7}$-alkyl, halogen and halogen-$C_{1-7}$-alkyl;

or pharmaceutically acceptable salts thereof.

In one aspect, the invention relates to compounds of formula I, wherein $B^1$ is N and $B^2$ is $CR^9$ and $B^3$ is $CR^{10}$. These are compounds of formula I having the formula

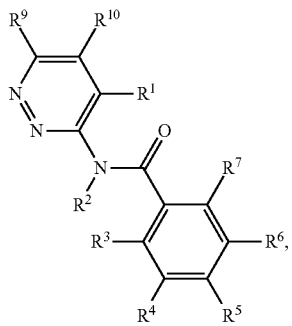

I-A wherein $R^1$ to $R^7$, $R^9$ and $R^{10}$ are as defined above.

In another aspect, the invention is concerned with compounds of formula I, wherein $B^1$ is $CR^8$ and $B^2$ is N and $B^3$ is $CR^{10}$. These are compounds of formula I having the formula

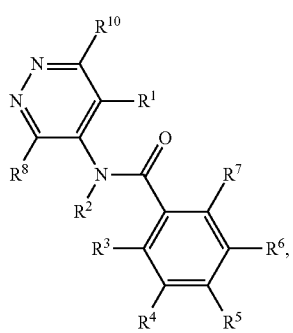

I-B wherein $R^1$ to $R^7$, $R^8$ and $R^{10}$ are as defined above.

In another aspect, the invention refers to compounds of formula I, wherein $B^1$ is $CR^8$ and $B^2$ is $CR^9$ and $B^3$ is N. These are compounds of formula I having the formula

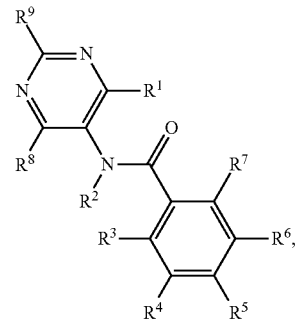

I-C wherein $R^1$ to $R^7$, $R^8$ and $R^9$ are as defined above.

In a further aspect, the invention relates to compounds of formula I, wherein $R^1$ is phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkyl, hydroxy-$C_{1-7}$-alkyl, hydroxy-$C_{1-7}$-alkoxy, $C_{1-7}$-alkoxy-$C_{1-7}$-alkyl, amino, $C_{1-7}$-alkylamino, di-$C_{1-7}$-alkylamino and phenyl-$C_{1-7}$-alkoxy.

In particular, the invention relates to compounds of formula I, wherein $R^1$ is phenyl, said phenyl being unsubstituted or substituted with one, two or three groups selected from the group consisting of $C_{1-7}$-alkyl, halogen and $C_{1-7}$-alkoxy. More particularly, $R^1$ is selected from phenyl, 4-fluoro-2-methoxy-phenyl and 4-o-tolyl.

In another aspect, the invention relates to compounds of formula I according to the invention, wherein $R^1$ is heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy.

In particular, the invention relates to compounds of formula I, wherein $R^1$ is heteroaryl, said heteroaryl being unsubstituted or substituted with one, two or three groups selected from the group consisting of $C_{1-7}$-alkoxy and halogen-$C_{1-7}$-alkoxy. More particularly, $R^1$ is pyridyl, said pyridyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy. Even more particularly, $R^1$ is 2-methoxy-pyridin-3-yl or 2-(2,2,2-trifluoroethoxy)-pyridin-3-yl.

In a further aspect, the invention relates to compounds of formula I, wherein $R^2$ is $C_{1-7}$-alkyl. In particular, the invention relates to compounds of formula I, wherein $R^2$ is methyl.

Furthermore, compounds of formula I according to the invention are in particular those, wherein $R^3$ and $R^7$ are hydrogen.

In another aspect, the invention relates to compounds of formula I, wherein $R^5$ is hydrogen.

In a further aspect, the invention relates to compounds of formula I, wherein at least one of $R^4$ and $R^6$ is selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxycarbonyl-$C_{1-7}$-alkylsulfonyl, heterocyclylsulfonyl, aminosulfonyl, $C_{1-7}$- alkylaminosulfonyl, di-($C_{1-7}$-alkyl)-aminosulfonyl, amino, $C_{1-7}$-alkylamino, di-($C_{1-7}$-alkyl)-amino, nitro, unsubstituted heterocyclyl or heterocyclyl substituted with one or two groups selected from halogen, oxo and $C_{1-7}$-alkyl.

Compounds of formula I according to the present invention are further those, wherein $R^4$ and $R^6$ are independently from each other selected from the group consisting of $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxycarbonyl-$C_{1-7}$-alkylsulfonyl, heterocyclylsulfonyl, aminosulfonyl, $C_{1-7}$-alkylaminosulfonyl, di-($C_{1-7}$-alkyl)-aminosulfonyl, amino, $C_{1-7}$-alkylamino, di-($C_{1-7}$-alkyl)-amino, nitro, unsubstituted heterocyclyl or heterocyclyl substituted with one or two groups selected from halogen, oxo and $C_{1-7}$-alkyl.

In particular, the invention relates to compounds of formula I, wherein $R^4$ and $R^6$ are independently from each other selected from the group consisting of $C_{1-7}$-alkyl, $C_{1-7}$-cycloalkyl, halogen, halogen-$C_{1-7}$-alkyl, $C_{1-7}$-alkylsulfonyl, carboxyl-$C_{1-7}$-alkylsulfonyl, $C_{1-7}$-alkoxycarbonyl-$C_{1-7}$-alkylsulfonyl and heterocyclylsulfonyl. More particularly, $R^4$ and $R^6$ are independently from each other selected from the group consisting of halogen-$C_{1-7}$-alkyl, $C_{1-7}$-alkylsulfonyl, carboxyl-$C_{1-7}$-alkylsulfonyl, $C_{1-7}$-alkoxycarbonyl-$C_{1-7}$-alkylsulfonyl and heterocyclylsulfonyl.

More particularly, compounds of formula I according to the invention are those, wherein $R^4$ is halogen-$C_{1-7}$-alkyl and $R^6$ is selected from the group consisting of $C_{1-7}$-alkylsulfonyl, carboxyl-$C_{1-7}$-alkylsulfonyl, $C_{1-7}$-alkoxycarbonyl-$C_{1-7}$-alkylsulfonyl, and heterocyclylsulfonyl. Even more particularly, $R^6$ is $C_{1-7}$-alkylsulfonyl.

Particular compounds of formula I according to the invention are the following:

N-[6-chloro-4-(4-fluoro-2-methoxy-phenyl)-pyridazin-3-yl]-3-methanesulfonyl-N-methyl-5-trifluoromethyl-benzamide,
N-[4-(4-fluoro-2-methoxy-phenyl)-pyridazin-3-yl]-3-methanesulfonyl-N-methyl-5-trifluoromethyl-benzamide,
N-[4-(4-fluoro-2-methoxy-phenyl)-6-methyl-pyridazin-3-yl]-3-methanesulfonyl-N-methyl-5-trifluoromethyl-benzamide,
N-(6-chloro-4-o-tolyl-pyridazin-3-yl)-3-methanesulfonyl-N-methyl-5-trifluoromethyl-benzamide,
N-(6-chloro-4-phenyl-pyridazin-3-yl)-3-methanesulfonyl-N-methyl-5-trifluoromethyl-benzamide,
N-(6-chloro-4-phenyl-pyridazin-3-yl)-3-methanesulfonyl-N-methyl-5-trifluoromethyl-benzamide,
N-(6-chloro-4-phenyl-pyridazin-3-yl)-N-methyl-3,5-bis-trifluoromethyl-benzamide
N-[6-chloro-4-(2-methoxy-pyridin-3-yl)-pyridazin-3-yl]-3-methanesulfonyl-N-methyl-5-trifluoromethyl-benzamide,
4-{3-[(6-chloro-4-o-tolyl-pyridazin-3-yl)-methyl-carbamoyl]-5-trifluoromethyl-benzenesulfonyl}-butyric acid tert-butyl ester,
4-{3-[(6-chloro-4-o-tolyl-pyridazin-3-yl)-methyl-carbamoyl]-5-trifluoromethyl-benzenesulfonyl}-butyric acid,
N-{6-chloro-4-[2-(2,2,2-trifluoro-ethoxy)-pyridin-3-yl]-pyridazin-3-yl}-3-methanesulfonyl-N-methyl-5-trifluoromethyl-benzamide,
3-methanesulfonyl-N-methyl-N-{4-[2-(2,2,2-trifluoro-ethoxy)-pyridin-3-yl]-pyridazin-3-yl}-5-trifluoromethyl-benzamide,
3-methanesulfonyl-N-methyl-N-{6-methyl-4-[2-(2,2,2-trifluoro-ethoxy)-pyridin-3-yl]-pyridazin-3-yl}-5-trifluoromethyl-benzamide,
N-[5-(4-fluoro-2-methoxy-phenyl)-pyridazin-4-yl]-3-methanesulfonyl-N-methyl-5-trifluoromethyl-benzamide,
3-methanesulfonyl-N-methyl-N-(5-o-tolyl-pyridazin-4-yl)-5-trifluoromethyl-benzamide,
3-chloro-5-methanesulfonyl-N-methyl-N-(5-o-tolyl-pyridazin-4-yl)-benzamide,
4-{3-[methyl-(5-o-tolyl-pyridazin-4-yl)-carbamoyl]-5-trifluoromethyl-benzenesulfonyl}-butyric acid tert-butyl ester,
4-{3-[methyl-(5-o-tolyl-pyridazin-4-yl)-carbamoyl]-5-trifluoromethyl-benzenesulfonyl}-butyric acid,
N-Methyl-N-(4-o-tolyl-pyrimidin-5-yl)-3,5-bis-trifluoromethyl-benzamide,
or pharmaceutically acceptable salts thereof.

More particularly, the invention relates to the following compounds of formula I:

N-[6-chloro-4-(4-fluoro-2-methoxy-phenyl)-pyridazin-3-yl]-3-methanesulfonyl-N-methyl-5-trifluoromethyl-benzamide,
N-[4-(4-fluoro-2-methoxy-phenyl)-6-methyl-pyridazin-3-yl]-3-methanesulfonyl-N-methyl-5-trifluoromethyl-benzamide,
N-[5-(4-fluoro-2-methoxy-phenyl)-pyridazin-4-yl]-3-methanesulfonyl-N-methyl-5-trifluoromethyl-benzamide,
or pharmaceutically acceptable salts thereof.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting an acid of the formula II

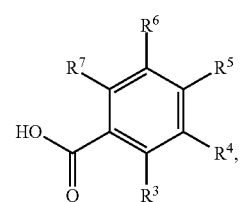

wherein $R^3$ to $R^7$ are as defined in claim 1, with an amine of the formula III

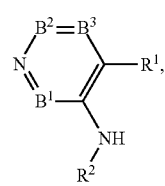

wherein $B^1$, $B^2$, $B^3$, $R^1$ and $R^2$ are defined in claim 1, in the presence of a coupling reagent to obtain a compound of the formula I

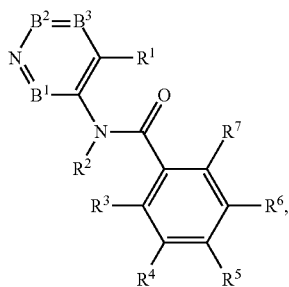

wherein $B^1$, $B^2$, $B^2$ and $R^1$ to $R^7$ are as defined in claim 1, and, if desired, converting the compound obtained into a pharmaceutically acceptable salt.

Appropriate coupling reagents are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), 2-chloro- or 2-bromo-1-methylpyridinium iodide (Mukaiyama reagent). Suitable solvents are for example N,N-dimethyl-formamide (DMF), dimethylacetamide (DMA), dichloromethane or dioxane, optionally in the presence of a base (e.g., triethylamine, N,N-diisopropylethylamine (Huenig's base) or 4-(dimethylamino)pyridine). The reaction is particularly carried out in the presence of a base such as for example triethylamine, N,N-diisopropylethylamine (Huenig's base) or 4-(dimethylamino)pyridine at temperatures between 0° C. and ambient temperature.

The invention further relates to compounds of formula I as defined above obtainable according to a process as defined above.

Compounds of the present invention can be prepared by various methods outlined in the exemplary reaction schemes below. For cases in which the starting materials and reagents used for the preparation of the compounds are commercially not available, they can be prepared by methods known to those skilled in the art and described in literature such as Fieser and Fieser's "Reagents for Organic Synthesis", Volumes 1-26, John Wiley & Sons, New York; M. B. Smith and J. March, "March's Advanced Organic Chemistry: Reactions, Mechanisms and Structure", $6^{th}$ edition, 2007, John Wiley & Sons, New York; S. Warren and P. Wyatt, "Organic Synthesis: The Disconnection Approach", $2^{nd}$ edition, 2008, John Wiley & Sons, New York; L. Kurti and B. Czako, "Strategic Applications of Named Reactions in Organic Synthesis", 2005, Elsevier Academic Press; B. M. Trost and Ian Fleming (editors), "Comprehensive Organic Synthesis", Volumes 1-8, Pergamon Press; J.-H. Fuhrhop and G. Li, "Organic Synthesis: Concepts and Methods", $3^{rd}$ edition, 2003, Wiley-VCH; "Strategies and Tactics in Organic Synthesis" Volumes 1-3 (T. Lindberg, editor) and 4-7 (M. Harmata, editor), Academic Press.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $4^{th}$ Ed., 2006, Wiley N.Y.) can be introduced before the critical step applying methods well known in the art. Such protecting groups can be removed at a later stage of the synthesis using standard methods described in the literature.

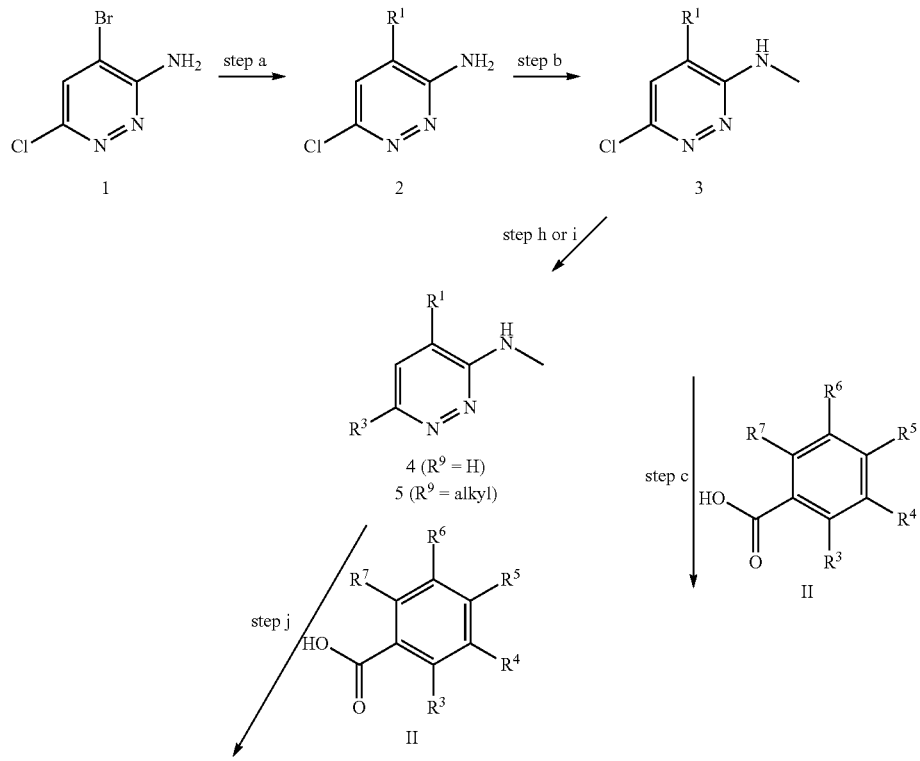

Scheme 1

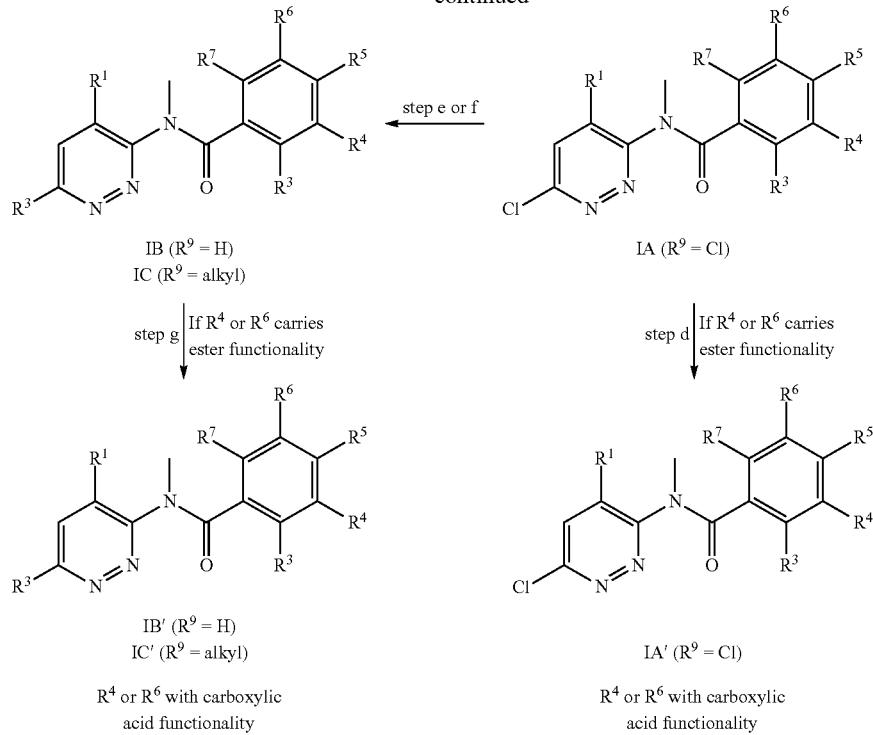

Compounds of general formula IA/IA' ($B^2$=$CR^9$ with $R^9$ being Cl), IB/IB' ($B^2$=$CR^9$ with $R^9$ being hydrogen) and IC/IC' ($B^2$=$CR^9$ with $R^9$ being lower alkyl) in which $B^1$=N, $B^3$=CH and $R^2$ is a methyl group can be prepared for example as outlined in Scheme 1.

For example, reaction of commercially available 4-bromo-6-chloro-pyridazin-3-ylamine 1 with (substituted) aryl- or heteroaryl-boronic acids $R^1$—$B(OH)_2$ or boronic esters $R^1$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) $1^{st}$ Ed., 2005, John Wiley & Sons, New York) using a suitable catalyst (e.g. dichloro[1,1-bis(diphenylphosphino)-ferrocene]palladium(II) dichloromethane adduct, tetrakis(triphenylphosphine)palladium(0) or palladium (II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates 2 (step a). Suzuki reactions of this type are broadly described in literature (e.g. M. Schmitt et al., Synlett 2003, 10, 1482-1484; A. Suzuki, Pure Appl. Chem. 1991, 63, 419-422; A. Suzuki, N. Miyaura, Chem. Rev. 1979, 95, 2457-2483; A. Suzuki, J. Organomet. Chem. 1999, 576, 147-168; V. Polshettiwar et al., Chem. Sus. Chem. 2010, 3, 502-522) and are well known to those skilled in the art. Alternatively, aryl- or heteroaryl-trifluoroborates $R^1BF_3K$ can be used in the cross-coupling reaction applying a palladium catalyst such as tetrakis-(triphenylphosphine)palladium(0), palladium(II) acetate or dichloro[1,1'-bis(diphenyl-phosphino)ferrocene]palladium (II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 2 can be also synthesized by reacting 1 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis(triphenylphosphine)-palladium(0), benzylbis(triphenyl-phosphine)palladium(II) chloride, bis(triphenylphosphine)-palladium(II) dichloride or dichloro[1,1'-bis(diphenylphosphino)ferrocene]palladium (II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, Angew. Chem. Int. Ed. Engl. 1986, 25, 508-524; V. Farina, J. Org. React. 1998, 50, 1-652; T. N. Mitchell, Synthesis 1992, 9, 803-815) and well known to those skilled in the art (step a).

Alternatively, intermediates 2 can be synthesized from reaction of 1 with (substituted) aryl- or heteroaryl zinc halides $R^1$—ZnX (X=Cl, Br or I) (either commercially available or synthesized by methods described in literature) using a nickel (e.g. tetrakis(triphenylphosphine)nickel(0)) or palladium catalyst (e.g. tetrakis(triphenyl-phosphine)palladium(0)) in an appropriate solvent such as THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley—VCH: Weinheim, Germany, 1998, 1-47; E. Erdik. Tetrahedron 1992, 48, 9577-9648; G. Organ, Eur. J. Org. Chem. 2010, 4343-4354) and well known to those skilled in the art (step a).

Intermediates 3 can be synthesized for example from intermediates 2 through reductive alkylation, e.g. by reacting 2 with trimethyl- or triethyl orthoformate in the presence of catalytic amounts of acid such as trifluoroacetic acid at elevated temperatures and reducing the in situ formed iminium species with a suitable reducing agent such as sodium borohydride or boran tetrahydrofuran complex at temperatures preferable between 0° C. and room temperature (step b).

Acylation of intermediates 3 with aryl carboxylic acids II (either commercially available or accessible by methods described in references or by methods known in the art) furnishes compounds IA (step c). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y., 1999) and can be accomplished by the usage of coupling reagents such as, e.g., N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethyl-formamide (DMF), dimethylacetamide (DMA), dichloromethane or dioxane, optionally in the presence of a base (e.g., triethylamine, N,N-diisopropylethylamine (Huenig's base) or 4-(dimethylamino)pyridine). Alternatively, the aryl carboxylic acids II can be converted into their acid chlorides by treatment with, e.g., thionyl chloride, neat or optionally in a solvent such as dichloromethane. Reaction of the acid chloride with amines 3 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture yields compounds IA (step c).

In those cases where the substituent $R^4$ or $R^6$ in compounds of formula IA carries an ester functionality, the ester functionality can be cleaved under basic (e.g. methyl or ethyl esters with lithium or sodium hydroxide in polar solvents such as methanol, water or tetrahydrofuran or mixtures of said solvents) or preferably under acidic conditions (e.g. a tert-butyl ester using concentrated hydrochloric acid in tetrahydrofuran or formic acid in an appropriate solvent such as alcohols like isopropanol) to furnish final compounds IA' (step d). Further esters include, but are not limited to, e.g. allyl or benzyl esters that can be cleaved by methods known to those skilled in the art and as described for example in "Protective Groups in Organic Chemistry" by T. W. Greene and P. G. M. Wuts, $4^{th}$ Ed., 2006, Wiley N.Y.)

Compounds of the general formula IB ($R^9$=H) can be synthesized for example by reduction of compounds IA using a variety of reducing systems well-known to those skilled in the art of chemical synthesis, for example, by hydrogenolysis using a suitable catalyst such as palladium on charcoal in an appropriate solvents or mixtures thereof such as alcohols (e.g. methanol, ethanol) or ethyl acetate under an atmosphere of hydrogen gas. Reactions of this type are broadly described in literature (e.g. E. A. Steck et al., *J. Am. Chem. Soc.*, 1954, 76, 3225-3226; P. Cioad et al., *J. Med. Chem.* 1965, 8, 129-31) and well known to those skilled in the art (step e).

Compounds of the general formula IC in which $R^9$ signifies an alkyl (e.g. a methyl, ethyl, propyl, isopropyl, isobutyl) or a cycloalkyl (e.g. a cyclopropyl) group can also be prepared from compounds IA. For example, reaction of compounds IA with (substituted) boronic acids $R^9$—$B(OH)_2$ or boronic esters $R^9$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) $1^{st}$ Ed., 2005, John Wiley & Sons, New York) using a suitable catalyst (e.g. dichloro[1,1-bis(diphenylphosphino)-ferrocene]palladium(II) dichloromethane adduct, tetrakis(triphenylphosphine)palladium(0) or palladium(II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields compounds IC (step f). Suzuki reactions of this type are broadly described in literature (e.g. WO 2011/017261; WO 2009/114677; A. Suzuki, *Pure Appl. Chem.* 1991, 63, 419-422; A. Suzuki, N. Miyaura, *Chem. Rev.* 1995, 95, 2457-2483; A. Suzuki, *J. Organomet. Chem.* 1999, 576, 147-168; V. Polshettiwar, *Chem. Sus. Chem.* 2010, 3, 502) and are well known to those skilled in the art.

Compounds IC can be also synthesized by reacting compounds IA with (substituted) alkyl tin reagents $R^9$—$SnR_3$ (R=e.g. Me or n-Bu; either commercially available or prepared according to literature procedures) in the presence of a suitable catalyst (e.g. tetrakis-(triphenylphosphine)-palladium(0), benzylbis(triphenylphosphine)-palladium(II) chloride, bis(triphenylphosphine)-palladium(II) dichloride or dichloro[1,1-bis(diphenylphosphino)-ferrocene]palladium (II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. WO 2008/097428; J. K. Stille, *Angew. Chem. Int. Ed. Engl.* 1986, 25, 508-524; V. Farina et al., *J. Org. React.* 1998, 50, 1-652; T. N. Mitchell, *Synthesis* 1992, 9, 803-815) and well known to those skilled in the art (step f). Alternatively, compounds IC can be synthesized from reaction of compounds IA with (substituted) alkyl zinc halides $R^9$—$ZnX$ (X=Cl, Br or I) (either commercially available or synthesized by methods described in literature) using a nickel (e.g. tetrakis(triphenylphosphine)nickel(0)) or palladium catalyst (e.g. tetrakis(triphenylphosphine)palladium (0)) in an appropriate solvent such as THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley—VCH: Weinheim, Germany, 1998, 1-47; E. Erdik, *Tetrahedron* 1992, 48, 9577-9648; G. Organ, *Eur. J. Org. Chem.* 2010, 23, 4343-4354) and well known to those skilled in the art (step f).

Alternatively, Grignard reactions, treating compounds IA with organomagnesium compounds of the type $R^9$—$MgX$ (X=Cl or Br) in an appropriate solvent such as tetrahydrofuran or NMP may be used to prepare compounds IC. Reactions of this type have also been described in literature (e.g. WO 2010/147430; F. Lamaty et al., *Synthetic Commun.* 2009, 39, 1583-1591) (step f).

Furthermore, compounds IA can be reacted with commercially available aluminum compounds of the type $(R^9)_3Al$ ($R^9$=Me, Et, iso-butyl) using an appropriate catalyst such, as e.g. tetrakis(triphenylphosphine)palladium(0), bis(triphenylphosphine)palladium(II) dichloride or tris(dibenzylideneacetone)dipalladium(0) in the presence of triphenylphosphine, in a suitable solvent such as dimethoxyethane, dioxane, toluene, hexane, DMF or mixtures thereof at temperatures ranging from room temperature to the boiling point of the solvent or solvent mixtures, to furnish compounds IC (step f). Reactions of this type have also been described in literature (e.g. WO 2009/015208; A. Cappelli et al., *ChemMedChem* 2010, 5, 739-748; M. J. Bamford et al., *Bioorg. Med. Chem. Lett.* 2005, 15, 3407-3411). In order to enhance the rate of conversion microwave-assisted heating might be applied.

In those cases where the substituent $R^2$ or $R^6$ in compounds of formula IB or IC carries an ester functionality, the ester functionality can be cleaved under basic (e.g. methyl or ethyl esters with lithium or sodium hydroxide in polar solvents such as methanol, water or tetrahydrofuran or mixtures of said solvents) or preferably under acidic conditions (e.g. a tert-butyl ester using concentrated hydrochloric acid in tetrahydrofuran or formic acid in an appropriate solvent such as alcohols like, e.g. isopropanol) to furnish final compounds IB' and IC', respectively (step g). Further esters include, but are not limited to, e.g. allyl or benzyl esters that can be cleaved by methods known to those skilled in the art and as described for example in "Protective Groups in Organic Chemistry" by T. W. Greene and P. G. M. Wuts, 4$^{th}$ Ed., 2006, Wiley N.Y.).

In those cases in which the ester functionality in substituents $R^4$ or $R^6$ is not stable under the reaction conditions applied for the synthesis of compounds IB and IC (steps e and f, respectively), intermediates 3 may be first converted into intermediates 4 or 5 (steps h and i, respectively), applying the same methods as described for steps e and f before. Acylation of intermediates 4 and 5 (step j) as described for the synthesis of compounds IA under step c then furnishes compounds IB and IC.

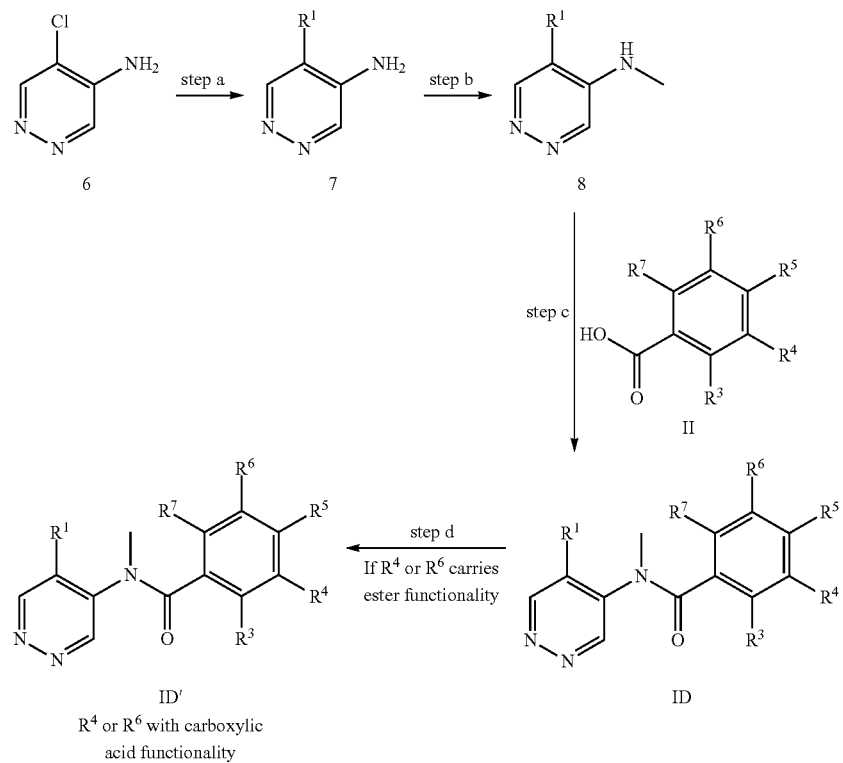

Scheme 2

Compounds of general formula ID and ID' in which $B^1$=CH, $B^2$=N, $B^3$=CH and $R^2$ is a methyl group can be prepared for example as outlined in Scheme 2.

For example, reaction of commercially available 5-chloropyridazin-4-ylamine 6 with (substituted) aryl- or heteroarylboronic acids $R^1$—B(OH)$_2$ or boronic esters $R^1$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1-bis(diphenylphosphino)-ferrocene]palladium(II) dichloromethane adduct, tetrakis(triphenylphosphine)palladium(0) or palladium (II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates 7 (step a). Suzuki reactions of this type are broadly described in literature (e.g. M. Schmitt et al., *Synlett* 2003, 10, 1482-1484; A. Suzuki, *Pure Appl. Chem.* 1991, 63, 419-422; A. Suzuki, N. Miyaura, *Chem. Rev.* 1979, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as tetrakis-(triphenylphosphine)palladium(0), palladium(II) acetate or dichloro[1,1'-bis(diphenyl-phosphino)ferrocene]palladium (II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Intermediates 7 can be also synthesized by reacting 6 with (substituted) aryl- or heteroaryl tin reagents $R^1$—SnR$_3$ (R=e.g. Me or n-Bu; either commercially available or prepared according to literature procedures) in the presence of a suitable catalyst (e.g. tetrakis(triphenylphosphine)-palladium(0), benzylbis(triphenyl-phosphine)palladium(II) chloride, bis(triphenylphosphine)-palladium(II) dichloride or dichloro[1,1'-bis(diphenylphosphino)ferrocene]palladium (II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina, *J. Org. React.* 1998, 50, 1-652; T. N. Mitchell, *Synthesis* 1992, 9, 803-815) and well known to those skilled in the art (step a).

Alternatively, intermediates 7 can be synthesized from reaction of 6 with (substituted) aryl- or heteroaryl zinc halides $R^1$—ZnX (X=Cl, Br or I) (either commercially available or synthesized by methods described in literature) using a nickel (e.g. tetrakis(triphenylphosphine)nickel(0)) or palladium catalyst (e.g. tetrakis(triphenyl-phosphine)palladium(0)) in an appropriate solvent such as THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley—VCH: Weinheim, Germany, 1998, 1-47; E. Erdik. *Tetrahedron* 1992, 48, 9577-9648; G. Organ, *Eur. J. Org. Chem.* 2010, 4343-4354) and well known to those skilled in the art (step a).

Intermediates 8 can be synthesized for example from intermediates 7 through reductive alkylation, e.g. by reacting 7 with trimethyl- or triethyl orthoformate in the presence of catalytic amounts of acid such as trifluoroacetic acid at elevated temperatures and reducing the in situ formed iminium species with a suitable reducing agent such as sodium borohydride or boran tetrahydrofuran complex at temperatures preferable between 0° C. and room temperature (step b).

Acylation of intermediates 8 with aryl carboxylic acids II (either commercially available or accessible by methods described in references or by methods known in the art) furnishes compounds ID (step c). Amide couplings of this type are widely described in the literature (e.g., Comprehensive Organic Transformations: A Guide to Functional Group Preparations, 2$^{nd}$ Edition, Richard C. Larock, John Wiley & Sons, New York, N.Y., 1999) and can be accomplished by the usage of coupling reagents such as N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethyl-formamide (DMF), dimethylacetamide (DMA), dichloromethane or dioxane, optionally in the presence of a base (e.g., triethylamine, N,N-diisopropylethylamine (Huenig's base) or 4-(dimethylamino)pyridine). Alternatively, the aryl carboxylic acids II can be converted into their acid chlorides by treatment with, e.g., thionyl chloride, neat or optionally in a solvent such as dichloromethane. Reaction of the acid chloride with amines 3 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture yields compounds ID.

In those cases where the substituent $R^4$ or $R^6$ in compounds of formula ID carries an ester functionality, the ester functionality can be cleaved under basic (e.g. methyl or ethyl esters with lithium or sodium hydroxide in polar solvents such as methanol, water or tetrahydrofuran or mixtures of said solvents) or preferably under acidic conditions (e.g. a tert-butyl ester using concentrated hydrochloric acid in tetrahydrofuran or formic acid in an appropriate solvent such as alcohols like isopropanol) to furnish final compounds ID' (step d). Further esters include, but are not limited to, e.g. allyl or benzyl esters that can be cleaved by methods known to those skilled in the art and as described for example in "Protective Groups in Organic Chemistry" by T. W. Greene and P. G. M. Wuts, 4$^{th}$ Ed., 2006, Wiley N.Y.).

Compounds of general formula IE and IE' in which $B^1=B^2=CH$, $B^3=N$ and $R^2$ is a methyl group can be prepared for example as outlined in Scheme 3.

For example, cross-coupling of commercially available 4,6-dichloro-5-nitro-pyrimidine 9 with (substituted) aryl- or heteroaryl-boronic acids $R^1$—B(OH)$_2$ or boronic esters $R^1$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1-bis(diphenylphosphino)-ferrocene]palladium(II) dichloromethane adduct, tetrakis(triphenylphosphine)palladium(0) or palladium (II) acetate with triphenylphosphine) in an appropriate solvent (e.g. dioxane, dimethoxyethane, water, toluene, N,N-dimethylformamide or mixtures thereof) and a suitable base (e.g. sodium carbonate, sodium hydrogen carbonate, potassium fluoride, potassium carbonate or triethylamine) at temperatures between room temperature and the boiling point of the solvent or solvent mixture yields intermediates 10 (step a). Suzuki reactions of this type are broadly described in literature (e.g. M. Schmitt et al., *Synlett* 2003, 10, 1482-1484; A. Suzuki, *Pure Appl. Chem.* 1991, 63, 419-422; A. Suzuki, N. Miyaura, *Chem. Rev.* 1979, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^1BF_3K$ can be used in the cross-coupling reaction applying a palladium catalyst such as tetrakis-(triphenylphosphine)palladium(0), palladium(II) acetate or dichloro[1,1'-bis(diphenyl-phosphino)ferrocene]palladium (II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

Scheme 3
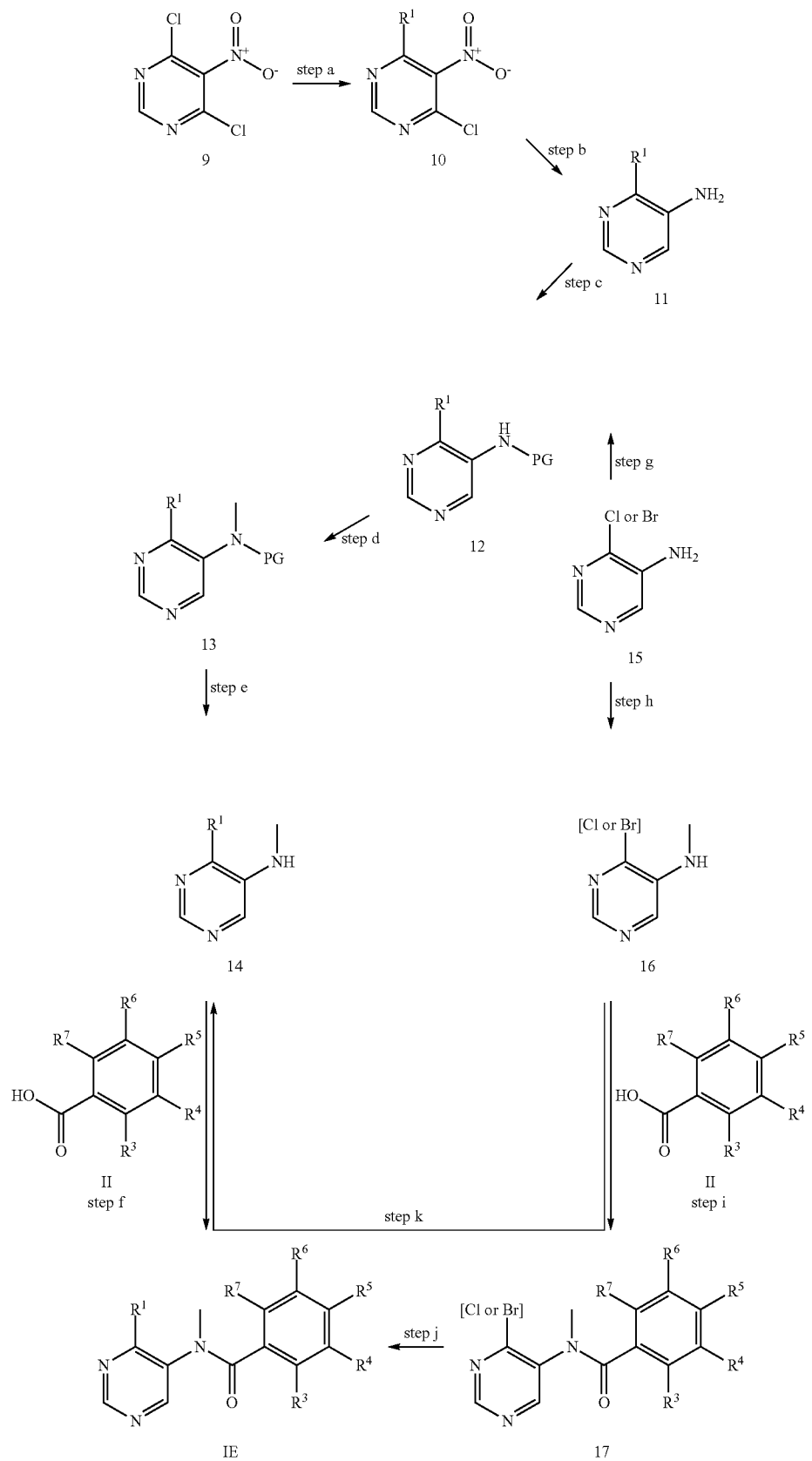

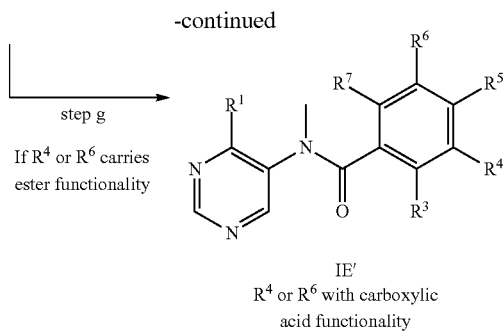

step g

If R⁴ or R⁶ carries ester functionality

IE'
R⁴ or R⁶ with carboxylic acid functionality

Intermediates 10 can be also synthesized by reacting 9 with (substituted) aryl- or heteroaryl tin reagents $R^1$—$SnR_3$ (R=e.g. Me or n-Bu; either commercially available or prepared according to literature procedures) in the presence of a suitable catalyst (e.g. tetrakis(triphenylphosphine)-palladium(0), benzylbis(triphenyl-phosphine)palladium(II) chloride, bis(triphenylphosphine)-palladium(II) dichloride or dichloro[1,1'-bis(diphenylphosphino)ferrocene]palladium (II) dichloromethane adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524; V. Farina, *J. Org. React.* 1998, 50, 1-652; T. N. Mitchell, *Synthesis* 1992, 9, 803-815) and well known to those skilled in the art (step a).

Alternatively, intermediates 10 can be synthesized from reaction of 9 with (substituted) aryl- or heteroaryl zinc halides $R^1$—ZnX (X=Cl, Br or I) (either commercially available or synthesized by methods described in literature) using a nickel (e.g. tetrakis(triphenylphosphine)-nickel(0)) or palladium catalyst (e.g. tetrakis(triphenyl-phosphine)palladium(0)) in an appropriate solvent such as THF or DMA in a temperature range between room temperature and boiling point of the solvent. Negishi couplings of this type are broadly described in literature (e.g. "Name Reactions for Homologations-Part I: Negishi cross-coupling reaction", Li, J. J., Corey, E. J., Eds.; Wiley & Sons, Hoboken, N.J., 2009, 70-99; "Metal-Catalyzed Cross-Coupling Reactions", Diederich, F.; Stang, P. J., Eds.; Wiley—VCH: Weinheim, Germany, 1998, 1-47; E. Erdik. *Tetrahedron* 1992, 48, 9577-9648; G. Organ, *Eur. J. Org. Chem.* 2010, 4343-4354) and well known to those skilled in the art (step a).

Reduction of intermediates 10 for example via hydrogenation (e.g. using a suitable catalyst such as palladium on carbon in an appropriate solvent such as MeOH, EtOH, EtOAc or mixtures thereof) gives amines 11 (step b). Alternatively, intermediates 11 can be prepared from commercially available 4-bromo- or 4-chloro-5-aminopyrimidine 15 applying metal-catalyzed cross-coupling reactions as described under step a before (step 1).

The amine group in intermediates 11 is protected for example with a tert-butyloxycarbonyl, 9-fluorenylmethyloxycarbonyl or pivaloyl protective group using methods described in literature to give intermediates 12 (step c).

Alkylation of 12 with $CH_3$-LG in which LG signifies a suitable leaving group such as bromo (or another leaving group such as chloro, iodo or $OSO_2$alkyl, $OSO_2$-fluoroalkyl, $OSO_2$aryl) using an appropriate base and solvent such as sodium hydride in tetrahydrofuran furnishes intermediates 13 (step d).

Removal of the protective group in intermediates 13 applying methods known to those skilled in the art and as described in literature (e.g. "Protective Groups in Organic Chemistry" by T. W. Greene and P. G. M. Wuts, $4^{th}$ Ed., 2006, Wiley N.Y.) gives intermediates 14 (step e).

Acylation of intermediates 14 with aryl carboxylic acids II (either commercially available or accessible by methods described in references or by methods known in the art) furnishes compounds IE (step f). Amide couplings of this type are widely described in the literature (e.g., Comprehensive Organic Transformations: A Guide to Functional Group Preparations, $2^{nd}$ Edition, Richard C. Larock, John Wiley & Sons, New York, N.Y., 1999) and can be accomplished by the usage of coupling reagents such as N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) or 2-chloro- or 2-bromo-1-methylpyridinium iodide (Mukaiyama reagent) in a suitable solvent, e.g., N,N-dimethyl-formamide (DMF), dimethylacetamide (DMA), dichloromethane or dioxane, optionally in the presence of a base (e.g., triethylamine, N,N-diisopropylethylamine (Huenig's base) or 4-(dimethylamino)pyridine). Alternatively, the aryl carboxylic acids II can be converted into their acid chlorides by treatment with, e.g., thionyl chloride, neat or optionally in a solvent such as dichloromethane. Reaction of the acid chloride with amines 3 in an appropriate solvent such as dichloromethane or DMF (N,N-dimethylformamide) and a base, e.g. triethylamine, N,N-diisopropylethylamine (Huenig's base), pyridine, 4-(dimethylamino)pyridine or lithium bis(trimethylsilyl)amide at temperatures ranging from ambient temperature to the reflux temperature of the solvent or solvent mixture yields compounds IE (step f).

In those cases where the substituent $R^4$ or $R^6$ in compounds of formula IE carries an ester functionality, the ester functionality can be cleaved under basic (e.g. methyl or ethyl esters with lithium or sodium hydroxide in polar solvents such as methanol, water or tetrahydrofuran or mixtures of said solvents) or preferably under acidic conditions (e.g. a tert-butyl ester using concentrated hydrochloric acid in tetrahydrofuran or formic acid in an appropriate solvent such as alcohols like, e.g. isopropanol) to furnish final compounds IE' (step g). Further esters include, but are not limited to, e.g. allyl or benzyl esters that can be cleaved by methods known to those skilled in the art and as described for example in "Protective Groups in Organic Chemistry" by T. W. Greene and P. G. M. Wuts, $4^{th}$ Ed., 2006, Wiley N.Y.).

Alternatively, compounds IE can also be prepared by metal-catalyzed cross-coupling of intermediates 17 with (substituted) aryl- or heteroaryl zinc halides, boronic acids or esters or stannanes (step j) applying the reaction methods as outlined before. Intermediates 17 in turn are accessible from intermediates 16 through acylation with aryl- or heteroaryl acids again using the conditions described before (step i). Intermediates 16 finally can be synthesized by alkylation of intermediates 15 with CH₃-LG (LG having the same meaning as defined before) (step h). To that end it can be advantageous to first protect the amine group in intermediates 15 with a protective group such as a tert-butoxycarbonyl group, which can be cleaved off after alkylation using methods known to those skilled in the art, as described in literature and as outlined before for the preparation of intermediates 14 from intermediates 11.

Intermediates 14 can also be obtained through cross-coupling of intermediates 16 with (substituted) aryl- or heteroaryl zinc halides, boronic acids or esters or stannanes applying the reaction methods as outlined above (step k).

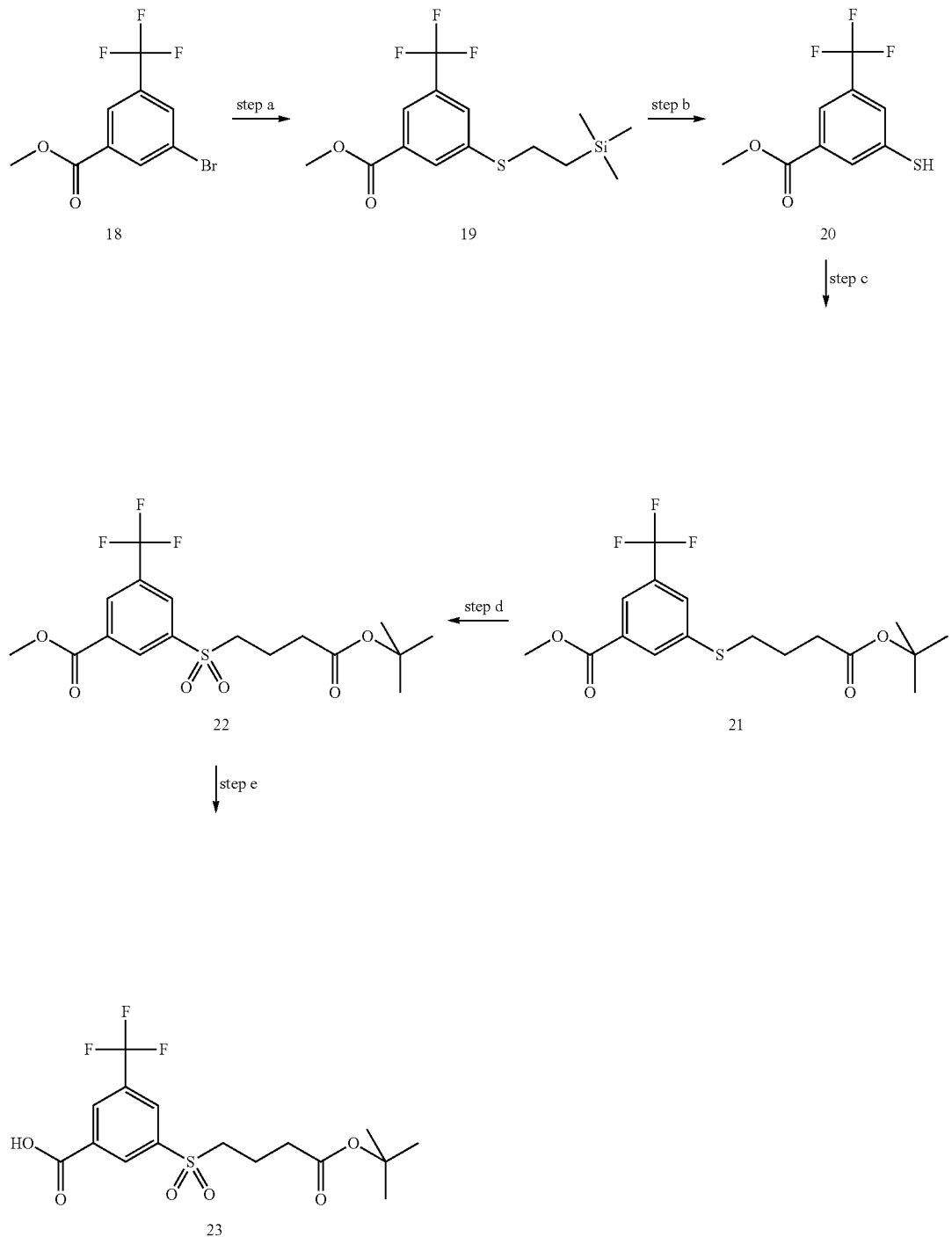

Scheme 4

If aryl carboxylic acids II are commercially not available they can be prepared by methods described in literature and known to those skilled in the art. For example, the carboxylic acid 23 can be prepared according to Scheme 4.

Cross-coupling of commercially available 3-bromo-5-trifluoromethyl-benzoic acid methyl ester 18 with 2-(trimethylsilyl)ethanethiol using a suitable catalytic system such as tris(dibenzylideneacetone)dipalladium(0)/Xantphos in the presence of a base such as diisopropylethylamine in a suitable solvent like dioxane, preferably at elevated temperatures, yields the thioether intermediate 19 (step a). Cleavage of the trimethylsilylethyl group in 19 with, e.g. tetrabutylammonium fluoride in tetrahydrofuran gives thiol 20 (step b). Reactions of this type have been described in literature, for example in WO2008055847. Alkylation of the thiol group in 20 with commercially available 4-bromo-butyric acid tert-butyl ester using an appropriate base and solvent such as triethyl- or diisopropylethyl-amine in acetonitrile or N,N-dimethylformamide, furnishes intermediate 21 (step c). The oxidation of the sulfur atom with oxidizing agents such as Oxone® in suitable solvents such as methanol or water or a mixture of said solvents leads to the aryl sulfonyl compound 22 (step d). Cleavage of the tert-butyl ester group using for example concentrated hydrochloric acid in tetrahydrofuran or formic acid in an appropriate solvent such as alcohols like, e.g. isopropanol, furnishes acid intermediate 23 (step e).

Yet another example for the synthesis of an aryl carboxylic acid II is shown in Scheme 5.

Scheme 5

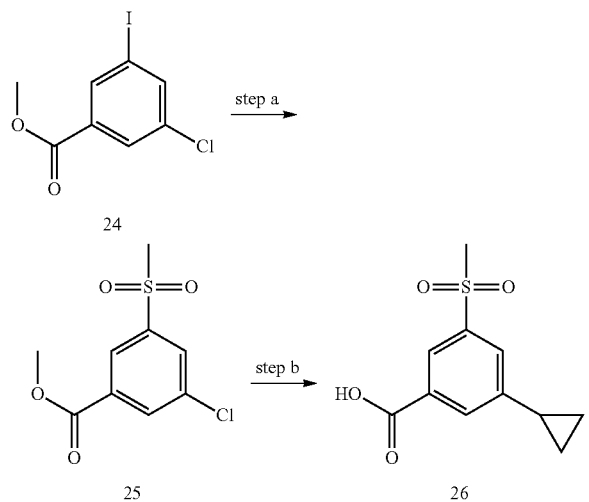

The iodine in commercially available methyl 3-chloro-5-iodobenzoate 24 can be exchanged for a methylsulfone group to give intermediate 25 (step a). Reactions of this type have been described in the literature (e.g. W. Zhu, D. Ma *J. Org. Chem.* 2005, 70(7), 2696-2700). For example, reaction of 24 with sodium methanesulfinate in the presence of a metal catalyst such as copper(I)iodide, L-proline and a base such as sodium hydroxide in an appropriate solvent such as DMSO gives intermediate 25. Heating may be applied to facilitate the reaction.

The chloro group in intermediate 25 can be converted into a cyclopropyl group using for example cyclopropylzinc(II) bromide in the presence of a suitable catalyst system such as PEPPSI-IPr ([1,3-bis(2,6-diisopropylphenyl)imidazol-2-ylidene](3-chloropyridyl)palladium(II) dichloride) with 1,3-dimethyl-2-imidazolidinone in a solvent such as tetrahydrofuran, preferably at higher temperatures up to the boiling point of the solvent to give intermediate 26. Pd-catalyzed reactions of that type using cyclopropylzinc bromide have been described in the literature (e.g. WO2008154271; WO2010011316). Under the applied reaction conditions, cleavage of the methyl ester may occur to give directly intermediates 56. If no ester cleavage occurs under the applied reaction conditions, the ester group can be cleaved by methods known in the art and as described for example in "Protective Groups in Organic Chemistry" by T. W. Greene and P. G. M. Wuts, 4$^{th}$ Ed., 2006, Wiley N.Y.) to give compounds 26 (step b).

As described herein before, the compounds of formula I of the present invention can be used as medicaments for the treatment of diseases which are associated with the modulation of GPBAR1 activity.

As compounds of formula I of the invention are agonists of the GPBAR1 receptor, the compounds will be useful for lowering glucose, lipids, and insulin resistance in diabetic patients and in non-diabetic patients who have impaired glucose tolerance or who are in a pre-diabetic condition. The compounds of formula I are further useful to ameliorate hyperinsulinemia, which often occurs in diabetic or pre-diabetic patients, by modulating the swings in the level of serum glucose that often occurs in these patients. The compounds of formula I are also useful in reducing the risks associated with metabolic syndrome, in reducing the risk of developing atherosclerosis or delaying the onset of atherosclerosis, and reducing the risk of angina, claudication, heart attack, stroke, and coronary artery disease. By keeping hyperglycemia under control, the compounds are useful to delay or for preventing vascular restenosis and diabetic retinopathy.

The compounds of formula I of the present invention are useful in improving or restoring β-cell function, so that they may be useful in treating type 1 diabetes or in delaying or preventing a patient with type 2 diabetes from needing insulin therapy. The compounds may be useful for reducing appetite and body weight in obese subjects and may therefore be useful in reducing the risk of co-morbidities associated with obesity such as hypertension, atherosclerosis, diabetes, and dyslipidemia. By elevating the levels of active GLP-1 in vivo, the compounds are useful in treating neurological disorders such as Alzheimer's disease, multiple sclerosis, and schizophrenia.

Thus, the expression "diseases which are associated with the modulation of GPBAR1 activity" means diseases such as metabolic, cardiovascular, and inflammatory diseases, for example diabetes, particularly type 2 diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, crohn's disease, disorders associated with parenteral nutrition especially during small bowel syndrome, irritable bowel syndrome (IBS), allergy diseases, fatty liver (e.g. non-alcoholic fatty liver disease, NAFLD), liver fibrosis (e.g. non-alcoholic steatohepatitis, NASH), primary sclerosing cholangitis (PSC), liver cirrhosis, primary biliary cirrhosis (PBC), liver colestasis, kidney fibrosis, anorexia nervosa, bulimia nervosa and neurological disorders such as Alzheimer's disease, multiple sclerosis, schizophrenia and impaired cognition.

In a particular aspect, the expression "diseases which are associated with the modulation of GPBAR1 activity" relates to diabetes, particularly type 2 diabetes, gestational diabetes, impaired fasting glucose, impaired glucose tolerance, hyperglycemia, metabolic syndrome, obesity, hypercholesterolemia and dyslipidemia.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the modulation of GPBAR1 activity.

Further, the invention relates to compounds of formula I as defined above for use as therapeutically active substances, particularly as therapeutically active substances for the treatment of diseases which are associated with the modulation of GPBAR1 activity. In particular, the invention relates to compounds of formula I for use in diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for use in diabetes, preferably type 2 diabetes, gestational diabetes or hyperglycemia.

In another aspect, the invention relates to a method for the treatment a of diseases which are associated with the modulation of GPBAR1 activity, which method comprises administering a therapeutically active amount of a compound of formula I to a human being or animal. In particular, the invention relates to a method for the treatment of diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for the treatment of diabetes, preferably type 2 diabetes, gestational diabetes or hyperglycemia.

The invention further relates to the use of compounds of formula I as defined above for the treatment of diseases which are associated with the modulation of GPBAR1 activity.

In addition, the invention relates to the use of compounds of formula I as defined above for the preparation of medicaments for the treatment of diseases which are associated with the modulation of GPBAR1 activity. In particular, the invention relates to the use of compounds of formula I as defined above for the preparation of medicaments for the treatment of diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for the preparation of medicaments for the treatment of diabetes, preferably type 2 diabetes, gestational diabetes or hyperglycemia.

Also contemplated herein is a combination therapy using one or more compounds of formula I or compositions of the present invention, or a pharmaceutically acceptable salts thereof, in combination with one or more other pharmaceutically active compounds independently selected from the group consisting of the following:

(a) human peroxisome proliferator activated receptor (PPAR) gamma agonists (e.g., thiazolidinediones and glitazones, e.g., rosiglitazone, troglitazone, pioglitazone, englitazone, balaglitazone, and netoglitazone), (b) biguanides such as metformin, metformin hydrochloride, buformin and phenformin, (c) dipeptidyl peptidase IV (DPP-4) inhibitors, such as sitagliptin, sitagliptin phosphate, saxagliptin, vildagliptin, alogliptin, carmegliptin, and denagliptin, (d) incretins such as glucagon-like peptide-1 (GLP-1) receptor agonists such as exenatide (Byetta™), liraglutide (Victoza™), GLP-1 (7-36) amide and its analogs, GLP-1 (7-37) and its analogs, AVE-0010 (ZP-10), R1583 (taspoglutide), GSK-716155 (albiglutide, GSK/Human Genome Sciences), BRX-0585 (Pfizer/Biorexis) and CJC-1134-PC (Exendin-4: PC-DAC™) or glucose-dependent insulinotropic peptide (GIP), (e) insulin or insulin analogs such as LysPro insulin or inhaled formulations comprising insulin, (f) sulfonylureas such as tolazamide, chlorpropamide, glipizide, glimepiride, glyburide, glibenclamide, tolbutamide, acetohexamide or glypizide, (g) α-glucosidase inhibitors such as miglitol, acarbose, epalrestat, or voglibose, (h) cholesterol biosynthesis inhibitors such as HMG CoA reductase inhibitors, e.g., lovastatin, simvastatin, pravastatin, fluvastatin, atorvastatin, rosuvastatin, cerivastatin, itavastin, nisvastatin and rivastatin, or squalene epoxidase inhibitors, e.g., terbinafine, (i) plasma HDL-raising agents such as CETP inhibitors e.g., anacetrapib, torcetrapib and dalcetrapib, or PPAR alpha agonists, e.g., gemfibrozil, clofibrate, fenofibrate and bezafibrate, (j) PPAR dual alpha/gamma agonists such as muraglitazar, naveglitazar, aleglitazar, tesaglitazar, peliglitazar, farglitazar and JT-501, (k) bile acid sequestrants, e.g., anion exchange resins, or quaternary amines (e.g., cholestyramine or colestipol)), or ileal bile acid transporter inhibitors (BATi);

(l) nicotinyl alcohol, nicotinic acid, niacinamide or salts thereof, (m) cholesterol absorption inhibitors such as ezetimibe or acyl-Coenzyme A:cholesterol O-acyl transferase (ACAT) inhibitors such as avasimibe, (n) selective estrogen receptor modulators such as raloxifene or tamoxifen) or LXR alpha or beta agonists, antagonists or partial agonists (e.g., 22(R)-hydroxycholesterol, 24(S)-hydroxycholesterol, T0901317 or GW3965);

(o) microsomal triglyceride transfer protein (MTP) inhibitors, alpha2-antagonists and imidazolines (e.g., midaglizole, isaglidole, deriglidole, idazoxan, efaroxan, fluparoxan), (p) insulin secretagogues such as linogliride, nateglinide, repaglinide, mitiglinide calcium hydrate or meglitinide);

(q) SGLT-2 inhibitors (e.g., dapagliflozin, sergliflozin and tofoglifozin), (s) glucokinase activators such as the compounds disclosed in e.g., WO 00/58293 A1;

(t) protein tyrosine phosphatase-1B (PTP-1B) inhibitors, (u) glucagon receptor antagonists, (v) anti-obesity agents such as fenfluramine, dexfenfluramine, phentiramine, sibutramine, orlistat, neuropeptide Y1 or Y5 antagonists, neuropeptide Y2 agonists, MC4R (melanocortin 4 receptor) agonists, cannabinoid receptor 1 (CB-1) antagonists/inverse agonists, and β3 adrenergic receptor agonists (e.g., GW-320659), nerve growth factor agonist (e.g., axokine), growth hormone agonists (e.g., AOD-9604), 5-HT (serotonin) reuptake/transporter inhibitors (e.g., Prozac), DA (dopamine) reuptake inhibitors (e.g., Buprorion), 5-HT, NA and DA reuptake blockers, steroidal plant extracts (e.g., P57), CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g., SNAP 7941), MCH2R (melanin concentrating hormone 2R) agonist/antagonists, H3 (histamine receptor 3) inverse agonists or antagonists, H1 (histamine 1 receptor) agonists, FAS (fatty acid synthase) inhibitors, ACC-2 (acetyl-CoA carboxylase-1) inhibitors, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), Topiramate, glucocorticoid antagonist, $5-HT_{2C}$ (serotonin receptor 2C) agonists (e.g., Lorcaserin), PDE (phosphodiesterase) inhibitors, fatty acid transporter inhibitors, dicarboxylate transporter inhibitors, glucose transporter inhibitors, (w) anti-inflammatory agents such as cyclooxygenase-2 (COX-2) inhibitors (e.g., rofecoxib and celecoxib); glucocorticoids, azulfidine, thrombin inhibitors (e.g., heparin, argatroban, melagatran, dabigatran) and platelet aggregation inhibitors (e.g., glycoprotein IIb/IIIa fibrinogen receptor antagonists or aspirin), and ursodeoxycholic acid (UDCA) and norursodeoxycholic acid (norUDCA) and (y) antihypertensives such as beta blockers (e.g., angiotensin II receptor antagonists such as losartan, eprosartan, irbesartan, tasosartan, telmisartan or valsartan; angiotensin converting enzyme inhibitors such as enalapril, captopril, cilazapril, ramapril, zofenopril, lisinopril and fosinopril; calcium channel blockers such as nifedipine and diltiazam and endothelian antagonists.

Such other pharmaceutically active compounds may be administered in an amount commonly used therefore, contemporaneously or sequentially with a compound of the formula I or a pharmaceutically acceptable salt thereof. In the treatment of patients who have type 2 diabetes, insulin resistance, obesity, metabolic syndrome, neurological disorders, and co-morbidities that accompany these diseases, more than one pharmaceutically active compound is commonly administered. The compounds of formula I of this invention may generally be administered to a patient who is already taking one or more other drugs for these conditions. When a compound of formula I is used contemporaneously with one or more other pharmaceutically active compounds, a pharmaceutical composition in an unit dosage form containing such other pharmaceutically active compounds and the compound of the formula I is preferred. Thus, the invention also relates to a pharmaceutical composition containing a compound of formula I in combination with one or more other pharmaceutically active compounds as defined above. When used in combination with one or more other active ingredients, the compound of formula I of the present invention and the other pharmaceutically active compounds may be used in lower doses than when each is used singly. These kinds of pharmaceutical compositions are also included in the invention.

However, the combination therapy also includes therapies in which the compound of formula I and one or more other pharmaceutically active compounds are administered in different dosage forms, but with overlapping schedules. The invention thus also relates to a method for the treatment a of diseases which are associated with the modulation of GPBAR1 activity, which method comprises administering a therapeutically active amount of a compound of formula I in combination with one or more other pharmaceutically active compounds to a human being or animal.

Pharmacological Test

The following test was carried out in order to determine the activity of the compounds of formula I:

The cDNA of the human GPBAR1 receptor (Genbank: NM 170699 with the exception of a silent C:G mutation at position 339 from the start codon) was amplified by polymerase chain reaction (PCR) from human cDNA and inserted into pCineo (Promega) by standard methods (Current Protocols in Molecular Biology, Wiley Press, ed. Ausubel et al.). The final clone was verified by DNA sequence analysis. The plasmid was transfected into CHO cells deficient in dihydrofolate reductase activity (CHO-dhfr−) using Lipofectamine plus (Invitrogen). Clones were isolated in limited dilution conditions and identified by activities in the cAMP assay using lithocholic acid as agonist. A clonal cell line displaying the greatest activity in cAMP increases was selected and identified as giving consistently good responses for up to at least 20 passages.

cAMP Assay

CHO-dhfr(minus) cells expressing human GPBAR1 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. The assay was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaked for 2 h at room temperature. The time-resolved energy transfer is measured by a TRF reader (Evotec Technologies GmbH, Hamburg Germany), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The measured signal at 730 nm has to be corrected for the ruthenium background, the direct excitation of Alexa and the buffer control. The FRET signal is calculated as follows: FRET=T730−Alexa730−P (T645−B645) with $P=R^{u730}$−B730/Ru645−B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of bile acids generated from this assay were in agreement with the values published in the scientific literature. Specificity for GPBAR1 was tested in non-transfected CHO cells in the same assay as above.

The compounds according to formula I have an activity in the above assay ($EC_{50}$) preferably of 0.5 nM to 10 µM, more preferably of 0.5 nM to 1 µM and most preferably 0.5 nM to 100 nM.

For example, the following compounds showed the following human $EC_{50}$ values in the functional cAMP assay described above:

| Example | human EC$_{50}$ [μM] |
|---|---|
| 1 | 0.165 |
| 2 | 0.075 |
| 3 | 0.178 |
| 4 | 2.175 |
| 5 | 2.693 |
| 6 | 0.427 |
| 7 | 0.299 |
| 8 | 1.524 |
| 9 | 1.079 |
| 10 | 8.181 |
| 11 | 2.392 |
| 12 | 0.16 |
| 13 | 3.908 |
| 14 | 0.23 |
| 15 | 0.429 |
| 16 | 0.663 |
| 17 | 0.775 |
| 18 | >10 |
| 19 | 1.479 |

Pharmaceutical Compositions

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C5 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example C2

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| | |
|---|---|
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example C4

Soft gelatin capsules containing the following ingredients can be manufactured in a conventional manner:

| Capsule contents | |
|---|---|
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example C5

Sachets containing the following ingredients can be manufactured in a conventional manner:

| | |
|---|---|
| Compound of formula I | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavouring additives and filled into sachets.

The following examples serve to illustrate the present invention in more detail. They are, however, not intended to limit its scope in any manner.

EXAMPLES

Example 1

N-[6-Chloro-4-(4-fluoro-2-methoxy-phenyl)-pyridazin-3-yl]-3-methanesulfonyl-N-methyl-5-trifluoromethyl-benzamide

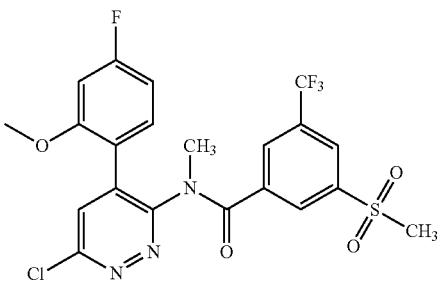

To a solution of [6-chloro-4-(4-fluoro-2-methoxy-phenyl)-pyridazin-3-yl]-methyl-amine (95 mg, 355 µmol) in dichloromethane (5 mL) was added 3-methanesulfonyl-5-trifluoromethyl-benzoic acid (95.2 mg, 355 mmol) and 2-bromo-1-ethylpyridinium tetrafluoroborate (117 mg, 426 µmol, CAS RN 878-23-9) and N-ethyldiisopropyl-amine (91.7 mg, 124 µL, 710 µmol). The reaction mixture was stirred at room temperature for 72 hours and then poured on 30 mL 10% aqueous bicarbonate solution and 30 mL dichloromethane and the layers were separated. The aqueous layer was extracted a second time with 30 mL dichloromethane. The organic layers were washed with 30 mL brine, dried over magnesium sulfate, filtered and concentrated under vacuum. The compound was purified by silica gel chromatography on a 20 g column using a MPLC system (CombiFlash Companion, Isco Inc.) eluting with a gradient of n-heptane:ethyl acetate (100:0 to 0:100). Colorless solid (63 mg, 34.3%). MS (ESI$^+$): m/z=518.056 ([M+H]$^+$).

Intermediates a) [6-Chloro-4-(4-fluoro-2-methoxy-phenyl)-pyridazin-3-yl]-methyl-amine To a solution of 6-chloro-4-(4-fluoro-2-methoxy-phenyl)-pyridazin-3-ylamine (300 mg, 1.18 mmol) in trimethyl orthoformate (1.00 g, 1.04 mL, 9.46 mmol) were added 2-3 drops of trifluoroacetic acid. The reaction mixture was stirred at reflux for 2 hours and then concentrated under vacuum. The residue was dissolved in 5 mL toluene and concentrated again under vacuum. This was repeated for three times to completely remove all volatiles. The residue was dissolved in tetrahydrofuran (3 mL) and borane tetrahydrofuran complex (1M solution, 2.96 mL, 2.96 mmol) was added in portions at 0° C. The reaction mixture was stirred at 90° C. for 2 hours and the resulting brown solution was cooled down to 0° C. and 25% aqueous hydrochloric acid (1 mL) was added slowly. The mixture was stirred at 90° C. for 1 hour and then poured on 30 mL water and 30 mL ethyl acetate. Aqueous sodium hydroxide solution (25%, 2 mL) was added and the layers were separated. The aqueous layer was extracted a second time with 30 mL ethyl acetate. The organic layers were washed with 30 mL brine, dried over magnesium sulfate, filtered and concentrated under vacuum. The compound was purified by silica gel chromatography on a 20 g column using a MPLC system (CombiFlash Companion, Isco Inc.) eluting with a gradient of n-heptane:ethyl acetate (100:0 to 0:100). Light yellow solid (119 mg, 37.6%). MS (ESI⁺): m/z=268.065 ([M+H]⁺).

b) 6-Chloro-4-(4-fluoro-2-methoxy-phenyl)-pyridazin-3-ylamine

To a solution of 4-bromo-6-chloropyridazin-3-amine (2.5 g, 12.0 mmol, CAS RN 446273-59-2) in 1,2-dimethoxyethane (30 mL) was added 4-fluoro-2-methoxyphenylboronic acid (2.45 g, 14.4 mmol, CAS RN 179899-07-1) and 2M aqueous sodium carbonate solution (10 mL). The reaction mixture was stirred under argon atmosphere for 15 minutes. Pd(II)acetate (135 mg, 600 μmol) and triphenylphosphine (315 mg, 1.2 mmol) was added. The dark red reaction mixture was stirred at 90° C. for 8 hours and then poured on 10% aqueous sodium bicarbonate solution (200 mL) and ethyl acetate (200 mL), filtered over dicalite and the layers were separated. The aqueous layer was extracted a second time with ethyl acetate (200 mL). The organic layers were washed with 200 mL brine, dried over magnesium sulfate, filtered and concentrated under vacuum. The residue was purified by silica gel chromatography on a 120 g column using a MPLC system (CombiFlash Companion, Isco Inc.) eluting with a gradient of n-heptane:ethyl acetate (100:0 to 0:100). Light red solid (1.71 g, 56.2%). MS (ESI⁺): m/z=254.050 ([M+H]⁺).

c) 3-Methanesulfonyl-5-trifluoromethyl-benzoic acid methyl ester

The mixture consisting of 1-bromo-3-(methylsulfonyl)-5-(trifluoromethyl)benzene (0.20 g, 0.66 mmol, Combi-Blocks, Inc.), 1,1'-bis(diphenylphosphino)ferrocene-palladium(II) dichloride dichloromethane complex (20.4 mg, 0.025 mmol, CAS RN 72287-26-4) and triethylamine (0.134 g, 0.184 mL, 1.32 mmol) in ethyl acetate (2 mL) and methanol (2 mL) was stirred at 110° C. under a 70 bar carbon monoxide atmosphere for 20 h. After cooling to room temperature silica gel was added and the brown suspension evaporated. The compound was purified by silica gel chromatography on a 20 g column using a MPLC system eluting with a gradient of n-heptane: ethyl acetate (100:0 to 50:50). Light brown oil (0.156 g; 83%). MS (GC_MS (EI)): m/z=282.0 [M].

d) 3-Methanesulfonyl-5-trifluoromethyl-benzoic acid

To a solution of 3-methanesulfonyl-5-trifluoromethyl-benzoic acid methyl ester (1.0 g, 3.54 mmol) in dioxane (15 mL) was added water (15 mL) and lithium hydroxide monohydrate (186 mg, 4.43 mmol). The reaction mixture was stirred at room temperature for 2 hours and then poured on 100 ml 1M aqueous hydrochloric acid and 100 mL ethyl acetate. The layers were separated and the aqueous layer was extracted a second time with 100 mL ethyl acetate. The organic layers were washed with 100 mL brine, dried over magnesium sulfate, filtered and concentrated under vacuum. Colorless solid (930 mg, 98%). MS (ESI⁻): m/z=266.995 ([M–H]⁻).

Example 2

N-[4-(4-Fluoro-2-methoxy-phenyl)-pyridazin-3-yl]-3-methanesulfonyl-N-methyl-5-trifluoromethyl-benzamide

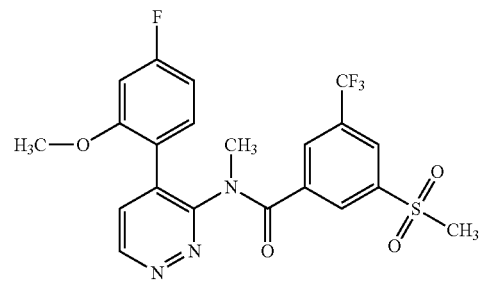

To a solution of N-[6-chloro-4-(4-fluoro-2-methoxy-phenyl)-pyridazin-3-yl]-3-methanesulfonyl-N-methyl-5-trifluoromethyl-benzamide (50 mg, 96.5 μmol, example 1) in methanol (2 mL) and ethyl acetate (2 mL) was added palladium on activated charcoal (10%, 10 mg, 96.5 μmol) under argon atmosphere. The reaction apparatus was evacuated and purged with hydrogen gas. The reaction was stirred under a hydrogen atmosphere of 1.7 bar for 8 hours. The reaction mixture was filtered over dicalite and the filtrate was concentrated under vacuum. The residue was purified by silica gel chromatography on a 10 g column using an MPLC (Flashmaster) system eluting with a gradient of n-heptane:ethyl acetate (100:0 to 0:100). The product was purified by preparative HPLC (Gemini NX column) with a gradient of methanol:water with 0.05% formic acid (80:20 to 98:2) to give the title compound as a light brown solid (13 mg, 27.9%). MS (ESI⁺): m/z=484.095 ([M+H]⁺).

Example 3

N-[4-(4-Fluoro-2-methoxy-phenyl)-6-methyl-pyridazin-3-yl]-3-methanesulfonyl-N-methyl-5-trifluoromethyl-benzamide

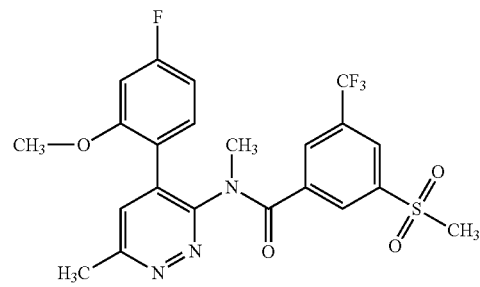

To a solution of N-[6-chloro-4-(4-fluoro-2-methoxy-phenyl)-pyridazin-3-yl]-3-methanesulfonyl-N-methyl-5-trifluoromethyl-benzamide (100 mg, 193 mmol, example 1) in tetrahydrofuran (2 mL) was added methylzinc chloride (2M solution in tetrahydrofuran, 145 μL, 290 mmol) and 1,3-dimethyl-2-imidazolidinone (400 μL, CAS RN 80-73-9) and PEPPSI-IPr (2.62 mg, 3.86 μmol, CAS RN 905459-27-0).

The reaction mixture was stirred at 60° C. for 5 hours, poured on 10% aqueous sodium bicarbonate solution (30 mL) and ethyl acetate (30 mL) and the layers were separated. The aqueous layer was extracted a second time with ethyl acetate (30 mL). The organic layers were washed with brine (30 mL), dried over magnesium sulfate, filtered and concentrated under vacuum. The compound was purified by silica gel chromatography on a 20 g column using an MPLC (Flashmaster) system eluting with a gradient of n-heptane:ethyl acetate (100:0 to 0:100). Light brown solid (70 mg, 72.9%). MS (ESI$^+$): m/z=498.110 ([M+H]$^+$).

Example 4

N-(6-Chloro-4-o-tolyl-pyridazin-3-yl)-3-methane-sulfonyl-N-methyl-5-trifluoromethyl-benzamide

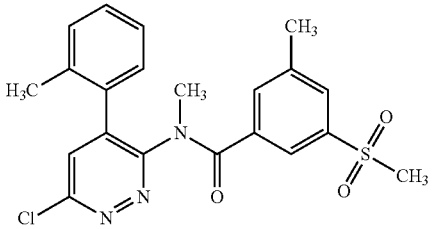

The title compound was prepared in analogy to example 1, from (6-chloro-4-o-tolyl-pyridazin-3-yl)-methyl-amine and 3-methanesulfonyl-5-trifluoromethyl-benzoic acid (example 1, intermediate d) after a reaction time of 18 hours, applying a second purification step using preparative HPLC (Gemini NX column) with a gradient of methanol:water with 0.05% formic acid (80:20 to 98:2). Colorless foam (23%). MS (ESI$^+$): m/z=484.070 ([M+H]$^+$).

Intermediates a) (6-Chloro-4-o-tolyl-pyridazin-3-yl)-methyl-amine

The title compound was prepared in analogy to example 1, intermediate a, from 6-chloro-4-o-tolyl-pyridazin-3-ylamine and using a gradient of n-heptane:ethyl acetate (100:0 to 0:70) eluant for the chromatographic purification. A second purification step on a 20 g column using an MPLC (Flashmaster) system (gradient of n-heptane:ethyl acetate (100:0 to 40:60)) furnished the title compound as a colorless solid (17%). MS (ESI$^+$): m/z=234.080 ([M+H]$^+$).

b) 6-Chloro-4-o-tolyl-pyridazin-3-ylamine

The title compound was prepared in analogy to example 1, intermediate b, from 4-bromo-6-chloropyridazin-3-amine (CAS RN 446273-59-2) and o-tolylboronic acid (CAS RN 16419-60-6). Light brown solid (41%). MS (ESI$^+$): m/z=220.064 ([M+H]$^+$).

Example 5

N-(6-Chloro-4-phenyl-pyridazin-3-yl)-3-methane-sulfonyl-N-methyl-5-trifluoromethyl-benzamide

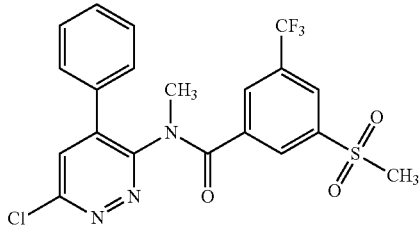 [SMILES: CN(C(=O)c1cc(C(F)(F)F)cc(S(C)(=O)=O)c1)c1nnc(Cl)cc1-c1ccccc1]

The title compound was prepared in analogy to example 1, from (6-chloro-4-phenyl-pyridazin-3-yl)-methyl-amine and 3-methanesulfonyl-5-trifluoromethyl-benzoic acid (example 1, intermediate d) after a reaction time of 18 hours and using a gradient of n-heptane:ethyl acetate (100:0 to 30:70) for the chromatographic purification. Another purification step using preparative HPLC (Gemini NX column) with a gradient of methanol:water with 0.05% formic acid (80:20 to 98:2) gave the desired compound as a colorless solid (20%). MS (ESI$^+$): m/z=470.054 ([M+H]$^+$).

a) (6-Chloro-4-phenyl-pyridazin-3-yl)-methyl-amine

The title compound was prepared in analogy to example 1, intermediate a, from 6-chloro-4-phenyl-pyridazin-3-ylamine and using a gradient of n-heptane:ethyl acetate (100:0 to 40:60) for the chromatographic purification. Light yellow solid (52%). MS (ESI$^+$): m/z=220.064 ([M+H]$^+$).

b) 6-Chloro-4-phenyl-pyridazin-3-ylamine

The title compound was prepared in analogy to example 1, intermediate b, from 4-bromo-6-chloropyridazin-3-amine (CAS RN 446273-59-2) and phenylboronic acid (CAS RN 98-80-6). Light yellow solid (38%). MS (ESI$^+$): m/z=206.048 ([M+H]$^+$).

Example 6

N-(6-Chloro-4-phenyl-pyridazin-3-yl)-3-methane-sulfonyl-N-methyl-5-trifluoromethyl-benzamide

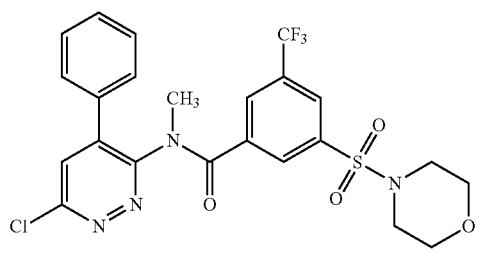 [SMILES: CN(C(=O)c1cc(C(F)(F)F)cc(S(=O)(=O)N2CCOCC2)c1)c1nnc(Cl)cc1-c1ccccc1]

The title compound was prepared in analogy to example 1, from (6-chloro-4-phenyl-pyridazin-3-yl)-methyl-amine (example 5, intermediate a) and 3-(morpholine-4-sulfonyl)-5-trifluoromethyl-benzoic acid and using a gradient of n-heptane:ethyl acetate (100:0 to 30:70) for the chromatographic purification. Another purification step using preparative HPLC (Gemini NX column) with a gradient of methanol:water with 0.05% formic acid (80:20 to 98:2) furnished the title compound as a colorless solid (14%). MS (ESI$^+$): m/z=541.090 ([M+H]$^+$).

Intermediates a) 3-(Morpholine-4-sulfonyl)-5-trifluoromethyl-benzoic acid

To a solution of 3-(morpholine-4-sulfonyl)-5-trifluoromethyl-benzoic acid methyl ester (1.04 g, 2.94 mmol) in dioxane (10 mL) was added water (10 mL) and lithium hydroxide monohydrate (154 mg, 3.68 mmol) and the resulting clear solution was stirred at room temperature for 2 hours. The reaction mixture was poured on 1M aqueous hydrochloric acid (100 mL) and 100 mL ethyl acetate and the layers were separated. The aqueous layer was extracted a second time with ethyl acetate (100 mL). The organic layers were washed with brine (100 mL), dried over magnesium sulfate, filtered and concentrated under vacuum to give the desired compound as a colorless solid (1 g, 100%) which was pure for the next step without further purification. MS (ESI$^-$): m/z=338.033 ([M−H]$^-$).

b) 3-(Morpholine-4-sulfonyl)-5-trifluoromethyl-benzoic acid methyl ester

To an ice-cold solution of methyl 3-(chlorosulfonyl)-5-(trifluoromethyl)benzoate (1.0 g, 3.3 mmol, Buttpark Ltd.) in dichloromethane (10 mL) was added N-ethyldiisopropylamine (854 mg, 1.15 mL, 6.61 mmol) and morpholine (317 mg, 317 µL, 3.63 mmol). The reaction mixture was stirred at room temperature for 2 hours, poured on 10% aqueous sodium bicarbonate solution (100 mL) and dichloromethane (100 mL) and the layers were separated. The aqueous layer was extracted a second time with dichloromethane (100 mL). The organic layers were washed with brine (100 mL), dried over magnesium sulfate, filtered and concentrated under vacuum. The compound was purified by silica gel chromatography on a 20 g column using a MPLC system (CombiFlash Companion, Isco Inc.) eluting with a gradient of n-heptane:ethyl acetate (100:0 to 35:65). Off-white solid (1.04 g, 89%). MS (EI): m/z=353.087 ([M]).

Example 7

N-(6-Chloro-4-phenyl-pyridazin-3-yl)-N-methyl-3,5-bis-trifluoromethyl-benzamide

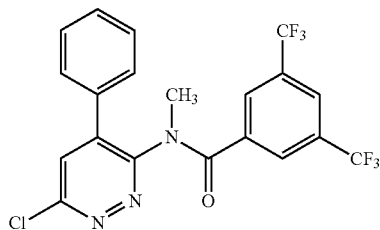 [SMILES: CN(C(=O)c1cc(C(F)(F)F)cc(C(F)(F)F)c1)c1nnc(Cl)cc1-c1ccccc1]

The title compound was prepared in analogy to example 1, from (6-chloro-4-phenyl-pyridazin-3-yl)-methyl-amine (example 5, intermediate a) and 3,5-bis(trifluoromethyl)benzoic acid (CAS RN 725-89-3) and using a gradient of n-heptane: ethyl acetate (100:0 to 30:70) for the chromatographic purification. Another purification step using preparative HPLC (Gemini NX column) with a gradient of methanol:water with 0.05% formic acid (80:20 to 98:2) yielded the compound as a colorless solid (5%). MS (ESI$^+$): m/z=460.064 ([M+H]$^+$).

Example 8

N-[6-Chloro-4-(2-methoxy-pyridin-3-yl)-pyridazin-3-yl]-3-methanesulfonyl-N-methyl-5-trifluoromethyl-benzamide

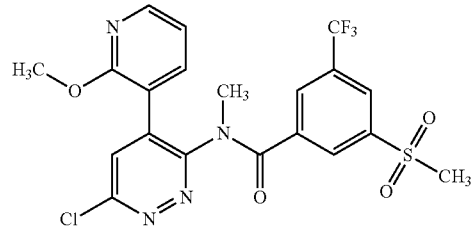

The title compound was prepared in analogy to example 1, from [6-chloro-4-(2-methoxy-pyridin-3-yl)-pyridazin-3-yl]-methyl-amine and 3-methanesulfonyl-5-trifluoromethyl-benzoic acid (example 1, intermediate d) after a reaction time of 27 hours and using a gradient of n-heptane:ethyl acetate (100:0 to 20:80) for the chromatographic purification. Light yellow solid (10%). MS (ESI$^+$): m/z=501.060 ([M+H]$^+$).

Intermediates a) [6-Chloro-4-(2-methoxy-pyridin-3-yl)-pyridazin-3-yl]-methyl-amine To a solution of 6-chloro-4-(2-methoxy-pyridin-3-yl)-pyridazin-3-ylamine (270 mg, 1.14 mmol) in triethyl orthoformate (6 mL) was added 1 drop of trifluoroacetic acid. The reaction mixture was stirred at 100° C. for 3 hours and then concentrated under vacuum (60° C./20 mbar). The residue was dissolved in 5 mL toluene and concentrated again. This was repeated for 3 times to completely remove all volatiles. The residue was dissolved in ethanol (6 mL) and sodium borohydride (86.3 mg, 2.28 mmol) was added in portions at 0° C. The reaction mixture was heated to 90° C. and stirred at this temperature for 2 hours. The reaction was cooled down to 0° C. and the pH was adjusted to 1 by addition of 0.25M aqueous sulfuric acid (5 mL). The yellow reaction mixture was stirred at room temperature for 3 hours, poured on 10% aqueous sodium bicarbonate solution (50 mL) and ethyl acetate (50 mL) (pH ca. 8) and the layers were separated. The aqueous layer was extracted a second time with ethyl acetate (50 mL). The organic layers were washed with brine (50 mL), dried over magnesium sulfate, filtered and concentrated under vacuum. The compound was purified by silica gel chromatography on a 20 g column using an MPLC (Flashmaster) system eluting with a gradient of n-heptane:ethyl acetate (100:0 to 0:100). Light yellow solid (100 mg, 35%). MS (ESI$^+$): m/z=251.069 ([M+H]$^+$).

b) 6-Chloro-4-(2-methoxy-pyridin-3-yl)-pyridazin-3-ylamine

The title compound was prepared in analogy to example 1, intermediate b, from 4-bromo-6-chloropyridazin-3-amine (CAS RN 446273-59-2) and 2-methoxypyridine-3-boronic acid (CAS RN 163105-90-6) after a reaction time of 18 hours. Brown solid (49%). MS (ESI$^+$): m/z=237.054 ([M+H]$^+$).

Example 9

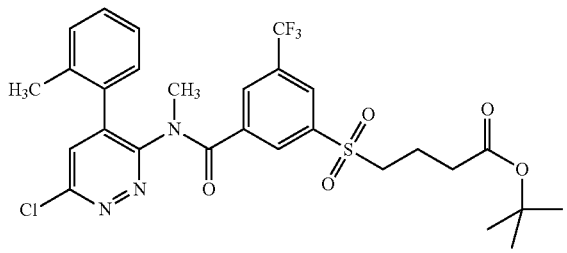 [SMILES: Cc1ccccc1-c1cc(Cl)nnc1N(C)C(=O)c1cc(C(F)(F)F)cc(S(=O)(=O)CCCC(=O)OC(C)(C)C)c1]

4-{3-[(6-Chloro-4-o-tolyl-pyridazin-3-yl)-methyl-carbamoyl]-5-methyl-benzenesulfonyl}-butyric acid tert-butyl ester The title compound was prepared in analogy to example 1, from (6-chloro-4-o-tolyl-pyridazin-3-yl)-methyl-amine (example 4, intermediate a) and 3-(3-tert-butoxycarbonyl-propane-1-sulfonyl)-5-trifluoromethyl-benzoic acid after a reaction time of 18 hours and using a gradient of n-heptane:ethyl acetate (100:0 to 30:70) for the chromatographic purification. Another purification step using preparative HPLC (Gemini NX column) with a gradient of methanol:water with 0.05% formic acid (80:20 to 98:2) yielded the desired compound as a colorless solid (14%). MS (ESI$^+$): m/z=541.090 ([M+H]$^+$).

Intermediates a) 3-(3-tert-Butoxycarbonyl-propane-1-sulfonyl)-5-trifluoromethyl-benzoic acid To a solution of 3-(3-tert-butoxycarbonyl-propane-1-sulfonyl)-5-trifluoromethyl-benzoic acid methyl ester (100 mg, 0.244 mmol) in dioxane (1 mL) was added water (1 mL) and lithiumhydroxide monohydrate (11.2 mg, 0.268 mmol) and the resulting suspension stirred at room temperature for 4 hours. The reaction mixture was acidified with 1M aqueous hydrochloric acid and extracted with EtOAc (30 mL) and the layers were separated. The aqueous layer was extracted a second time with EtOAc (30 mL). The organic layers were washed with brine (30 mL), dried over magnesium sulfate, filtered and concentrated under vacuum. Colorless solid (76 mg, 78.7%). MS (ESI$^-$): m/z=395.08 ([M–H]$^-$).

c) 3-(3-tert-Butoxycarbonyl-propane-1-sulfonyl)-5-trifluoromethyl-benzoic acid methyl ester To an ice-cold solution of 3-(3-tert-butoxycarbonyl-propylsulfanyl)-5-trifluoromethyl-benzoic acid methyl ester (1.24 g, 3.28 mmol) in methanol (28 mL) and water (7 mL) was added Oxone® (5.04 g, 8.19 mmol) and stirring was continued at room temperature for 95 hours. The reaction mixture was poured on 10% aqueous sodium thiosulfate solution and ethyl acetate and the layers were separated. The aqueous layer was extracted four times with ethyl acetate. The organic layers were washed once with brine, dried over magnesium sulfate, filtered and evaporated. The compound was purified by silica gel chromatography on a 50 g column using a MPLC system (CombiFlash Companion, Isco Inc.) eluting with a gradient of n-heptane:ethyl acetate (100:0 to 50:50) to furnish the title compound as a colorless oil (609 mg, 45%). MS (EI): m/z=410 ([M]).

d) 3-(3-tert-Butoxycarbonyl-propylsulfanyl)-5-trifluoromethyl-benzoic acid methyl ester To a solution of 3-mercapto-5-trifluoromethyl-benzoic acid methyl ester (990 mg, 4.19 mmol) in acetonitrile (25 mL) were added N,N-diisopropylethylamine (1.08 g, 1.46 mL, 8.38 mmol) and tert-butyl 4-bromobutanoate (935 mg, 4.19 mmol, CAS RN 110611-91-1). The clear yellow solution was stirred at room temperature for 2.5 hours and then poured on water and ethyl acetate and the layers were separated. The aqueous layer was extracted twice with ethyl acetate. The organic layers were washed with brine, dried over magnesium sulfate, filtered, treated with silica gel and evaporated. The compound was purified by silica gel chromatography on a 50 g column using a MPLC system (CombiFlash Companion, Isco Inc.) eluting with a gradient of n-heptane:ethyl acetate (100:0 to 70:30). Light yellow liquid (1.27 g, 80%). MS (ESI$^+$): m/z=379 ([M$^+$]).

e) 3-Mercapto-5-trifluoromethyl-benzoic acid methyl ester

To a solution of 3-trifluoromethyl-5-(2-trimethylsilanyl-ethylsulfanyl)-benzoic acid methyl ester (580 mg, 1.72 mmol) in tetrahydrofuran (15 mL) was added tetrabutylammonium fluoride (1M solution in tetrahydrofuran, 11.6 mL, 11.6 mmol) and the yellow solution was stirred at room temperature for 1 hour. The reaction mixture was poured on aqueous 1M hydrochloric acid (30 mL) and ethyl acetate (30 mL) and the layers were separated. The aqueous layer was extracted a second time with ethyl acetate (30 mL). The organic layers were washed with 30 mL brine, dried over magnesium sulfate, filtered and concentrated under vacuum. The compound was purified by silica gel chromatography on a 20 g column using a MPLC system (CombiFlash Companion, Isco Inc.) eluting with a gradient of n-heptane:ethyl acetate (100:0 to 0:100). Yellow solid (295 mg, 72%). MS (ESI$^-$): m/z=235.01 ([M–H]$^-$).

f) 3-Trifluoromethyl-5-(2-trimethylsilanyl-ethylsulfanyl)-benzoic acid methyl ester A solution of 3-bromo-5-trifluoromethyl-benzoic acid methyl ester (600 mg, 2.12 mmol, CAS RN 187331-46-0) in dioxane (6 mL) and 2-(trimethylsilyl)ethanethiol (285 mg, 335 µL, 2.12 mmol, CAS RN 18143-30-1) was stirred under argon for 5 min., treated with tris(dibenzylideneacetone)dipalladium (0) (48.5 mg, 53.0 µmol, CAS RN 52522-40-4), 4,5-bis(diphenylphosphino)-9,9-dimethylxanthene (61.3 mg, 106 µmol, xantphos, CAS RN 161265-03-8) and N,N-diisopropylethylamine (548 mg, 740 µL, 4.24 mmol) and stirred at 120° C. in a sealed tube for 4 h. Stirring was continued at room temperature for another 18 hours. The reaction mixture was poured on saturated aqueous ammonium chloride solution and ethyl acetate and the layers were separated. The aqueous layer was extracted twice with ethyl acetate. The organic layers were dried over magnesium sulfate, filtered, treated with silica gel and evaporated. The compound was purified by silica gel chromatography on a 20 g column using a MPLC system (CombiFlash Companion, Isco Inc.) eluting with a gradient of n-heptane:ethyl acetate (100:0 to 80:20). Yellow liquid (587 mg, 82%). MS (EI): m/z=336 ([M]).

Example 10

4-{3-[(6-Chloro-4-o-tolyl-pyridazin-3-yl)-methyl-carbamoyl]-5-trifluoromethyl-benzenesulfonyl}-butyric acid

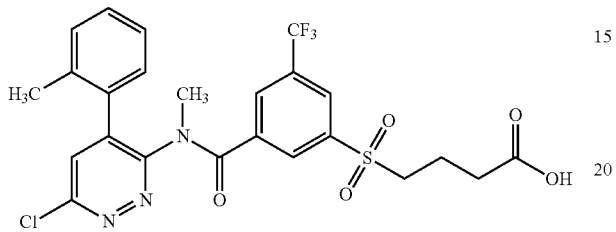

To a solution of 4-{3-[(6-chloro-4-o-tolyl-pyridazin-3-yl)-methyl-carbamoyl]-5-methyl-benzenesulfonyl}-butyric acid tert-butyl ester (0.055 g, 89.9 µmol) in dichloromethane (1.5 mL) were added anisole (10.7 mg, 10.8 µL, 98.8 µmol) and trifluoroacetic acid (512 mg, 346 µL, 4.49 mmol) and the light yellow solution was stirred at room temperature for 3.5 hours. The reaction mixture was evaporated to dryness and the residue treated with toluene and again completely evaporated. The product was purified by preparative HPLC (Gemini NX column) using a gradient of methanol:water (containing 0.1% formic acid) (20:80 to 98:2). Colorless foam (0.037 g; 74%). MS (ESI$^+$): m/z=556.09 ([M+H]$^+$).

Example 11

N-{6-Chloro-4-[2-(2,2,2-trifluoro-ethoxy)-pyridin-3-yl]-pyridazin-3-yl}-3-methanesulfonyl-N-methyl-5-trifluoromethyl-benzamide

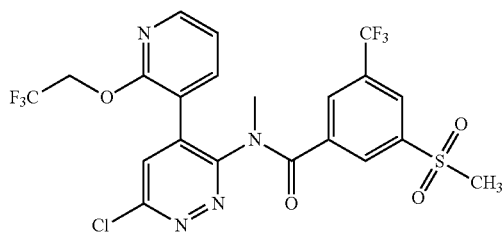 [SMILES: CN(C(=O)c1cc(C(F)(F)F)cc(S(C)(=O)=O)c1)c1nnc(Cl)cc1-c1cccnc1OCC(F)(F)F]

The title compound was prepared in analogy to example 1, from {6-chloro-4-[2-(2,2,2-trifluoro-ethoxy)-pyridin-3-yl]-pyridazin-3-yl}-methyl-amine and 3-methanesulfonyl-5-trifluoromethyl-benzoic acid (example 1, intermediate d) after a reaction time of 18 hours. Light yellow solid (13%). MS (ESI$^+$): m/z=560.048 ([M+H]$^+$).

Intermediates a) {6-Chloro-4-[2-(2,2,2-trifluo-ethoxy)-pyridin-3-yl]-pyridazin-3-yl}-methyl-amine The title compound was prepared in analogy to example 8, intermediate a, from 6-chloro-4-[2-(2,2,2-trifluoro-ethoxy)-pyridin-3-yl]-pyridazin-3-ylamine. Light yellow solid (45%). MS (ESI$^+$): m/z=319.057 ([M+H]$^+$).

b) 6-Chloro-4-[2-(2,2,2-trifluoro-ethoxy)-pyridin-3-yl]-pyridazin-3-ylamine

The title compound was prepared in analogy to example 1, intermediate b, from 4-bromo-6-chloro-pyridazin-3-ylamine (CAS RN 446273-59-2) and 2-(2,2,2-trifluoroethoxy)pyridine-3-boronic acid (CAS RN 1218790-79-4) after a reaction time of 18 hours. Brown solid (43%). MS (ESI$^+$): m/z=305.041 ([M+H]$^+$).

Example 12

3-Methanesulfonyl-N-methyl-N-{4-[2-(2,2,2-trifluoro-ethoxy)-pyridin-3-yl]-pyridazin-3-yl}-5-trifluoromethyl-benzamide

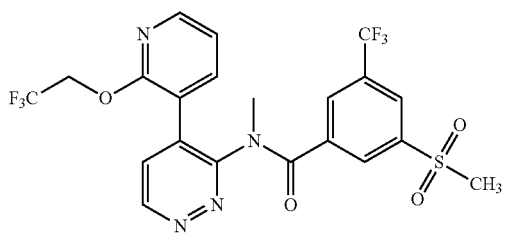 [SMILES: CN(C(=O)c1cc(C(F)(F)F)cc(S(C)(=O)=O)c1)c1nnccc1-c1cccnc1OCC(F)(F)F]

The title compound was prepared in analogy to example 2, from N-{6-chloro-4-[2-(2,2,2-trifluoro-ethoxy)-pyridin-3-yl]-pyridazin-3-yl}-3-methanesulfonyl-N-methyl-5-trifluoromethyl-benzamide (example 10), without further preparative HPLC purification. Colorless solid (14%). MS (ESI$^+$): m/z=535.087 ([M+H]$^+$).

Example 13

3-Methanesulfonyl-N-methyl-N-{6-methyl-4-[2-(2,2,2-trifluoro-ethoxy)-pyridin-3-yl]-pyridazin-3-yl}-5-trifluoromethyl-benzamide

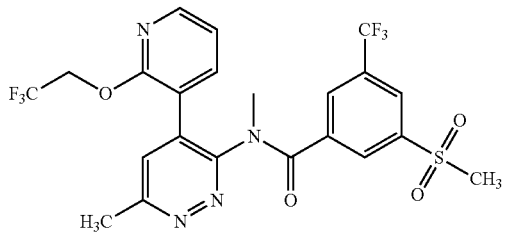 [SMILES: Cc1cc(-c2cccnc2OCC(F)(F)F)c(N(C)C(=O)c2cc(C(F)(F)F)cc(S(C)(=O)=O)c2)nn1]

The title compound was prepared in analogy to example 3, from N-{6-chloro-4-[2-(2,2,2-trifluoro-ethoxy)-pyridin-3-yl]-pyridazin-3-yl}-3-methanesulfonyl-N-methyl-5-trifluoromethyl-benzamide (example 10). A second purification step using preparative HPLC (Gemini NX column) with a gradient of methanol:water with 0.05% formic acid (80:20 to 98:2) furnished the title compound as a colorless solid (17%). MS (ESI+): m/z=594.102 ([M+H]+).

Example 14

N-[5-(4-Fluoro-2-methoxy-phenyl)-pyridazin-4-yl]-3-methanesulfonyl-N-methyl-5-trifluoromethyl-benzamide

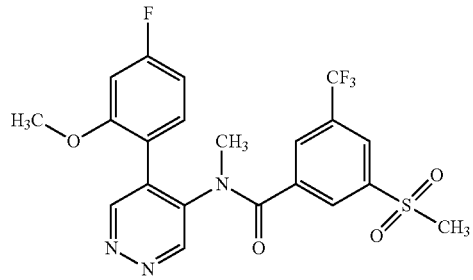

To a solution of 5-(4-fluoro-2-methoxyphenyl)-N-methylpyridazin-4-amine (27 mg, 116 µmol) in dichloromethane (1 mL) were added 3-(methylsulfonyl)-5-(trifluoromethyl) benzoyl chloride (66.4 mg, 232 mmol) and N,N-diisopropylethylamine (60 mg, 80.9 µL, 463 µmol). The clear, light brown solution was stirred at room temperature for 1.75 h and then poured on saturated aqueous ammonium chloride solution and dichloromethane and the layers were separated. The aqueous layer was extracted three times with dichloromethane. The organic layers were dried over magnesium sulfate, filtered, treated with silica gel and evaporated. The compound was purified by silica gel chromatography on a 10 g column using a MPLC system (CombiFlash Companion, Isco Inc.) eluting with a gradient of n-heptane:ethyl acetate (100:0 to 0:100) to give the desired compound as a light brown solid (15 mg; 25%). MS (ESI+): m/z=483.09 ([M+H]+).

Intermediates a) [5-(4-Fluoro-2-methoxy-phenyl)-pyridazin-4-yl]-methyl-amine

The title compound was prepared in analogy to example 1, intermediate a, from 5-(4-fluoro-2-methoxy-phenyl)-pyridazin-4-ylamine and using a gradient of dichloromethane:methanol (100:0 to 90:10) for the chromatographic purification. Brown oil (5%). MS (ESI+): m/z=234.1 ([M+H]+).

b) 5-(4-Fluoro-2-methoxy-phenyl)-pyridazin-4-ylamine

The title compound was prepared in analogy to example 1, intermediate b, from 5-chloro-pyridazin-4-ylamine (CAS RN 53180-92-0) and 4-fluoro-2-methoxyphenylboronic acid (CAS RN 179899-07-1) and using a gradient of n-heptane:ethyl acetate:methanol (100:0:0 to 0:100:0 to 0:50:50) for the chromatographic purification. Light yellow solid (37%). MS (ESI+): m/z=220.089 ([M+H]+).

c) 3-(Methylsulfonyl)-5-(trifluoromethyl)benzoyl chloride

To 3-(methylsulfonyl)-5-(trifluoromethyl)benzoic acid (1 g, 3.73 mmol, example 1, intermediate d) was added N,N-dimethylformamide (27.3 mg, 28.9 µL, 373 µmol) and thionyl chloride (8.87 g, 5.44 ml, 74.5 mmol) and the suspension was heated to reflux for 30 min. A light brown solution was formed. To remove thionyl chloride, the light brown solid was diluted with toluene, followed by complete evaporation. This procedure was repeated two times to provide the desired compound as a colorless solid (1.1 g; 99%) which was pure enough for the next step without further purification.

Example 15

3-Methanesulfonyl-N-methyl-N-(5-o-tolyl-pyridazin-4-yl)-5-trifluoromethyl-benzamide

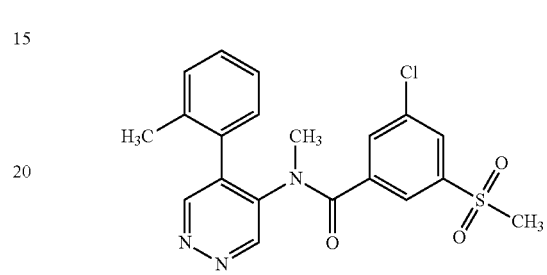

The title compound was prepared in analogy to example 1, from methyl-(5-o-tolyl-pyridazin-4-yl)-amine and 3-methanesulfonyl-5-trifluoromethyl-benzoic acid (example 1, intermediate d) after a reaction time of 18 hours. A second purification step using preparative HPLC (Gemini NX column) with a gradient of acetonitrile:water with 0.05% formic acid (80:20 to 98:2) furnished the title compound as a colorless solid (33%). MS (ESI+): m/z=450.109 ([M+H]+).

Intermediates a) Methyl-(5-o-tolyl-pyridazin-4-yl)-amine

The title compound was prepared in analogy to example 8, intermediate a, from 5-o-tolyl-pyridazin-4-ylamine and using a gradient of n-heptane:ethyl acetate (100:0 to 40:60) for the chromatographic purification. Light yellow solid (71%). MS (EI): m/z=199 ([M]).

b) 5-o-Tolyl-pyridazin-4-ylamine

The title compound was prepared in analogy to example 1, intermediate b, from 5-chloro-pyridazin-4-ylamine (CAS RN 53180-92-0) and 2-methylphenylboronic acid (CAS RN). Light yellow solid (37%). MS (ESI+): m/z=186.103 ([M+H]+).

Example 16

3-Chloro-5-methanesulfonyl-N-methyl-N-(5-o-tolyl-pyridazin-4-yl)-benzamide

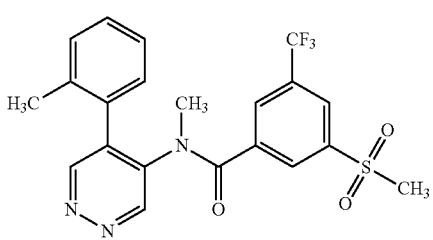

The title compound was prepared in analogy to example 1, from methyl-(5-o-tolyl-pyridazin-4-yl)-amine and 3-chloro-5-methanesulfonyl-benzoic acid. A second purification step using preparative HPLC (Gemini NX column) with a gradient of acetonitrile:water with 0.05% formic acid (80:20 to 98:2) gave the desired compound as a colorless solid (44%). MS (ESI⁺): m/z=416.083 ([M+H]⁺).

Intermediates a) 3-Chloro-5-methanesulfonyl-benzoic acid

To a solution of 3-chloro-5-methanesulfonyl-benzoic acid methyl ester (2.3 g, 9.25 mmol) in tetrahydrofuran (30 mL) and water (15 mL) was added lithium hydroxide monohydrate (1.164 g, 27.75 mmol) at 25° C. and the reaction mixture was stirred for 1 h. The solvent was evaporated, the residue dissolved in water (25 mL), acidified with 2M aqueous hydrochloric acid to pH 3 and extracted three times with ethyl acetate (40 mL each). The combined organic layers were washed with brine (50 mL), dried over anhydrous sodium sulfate and evaporated to afford the desired compound as a colorless solid (1.8 g, 83%). MS (ESI⁻): m/z=233.2 ([M−H]⁻).

b) 3-Chloro-5-methanesulfonyl-benzoic acid methyl ester

To a solution of L-proline (1.553 g, 13.49 mmol, CAS RN 147-85-3) in dimethylsulfoxide (80 mL) was added sodium hydroxide (0.54 g, 13.49 mmol) and the reaction mixture was stirred at 25° C. for 30 min. Then copper(I) iodide (2.568 g, 13.49 mmol), 3-chloro-5-iodo-benzoic acid methyl ester (5.0 g, 16.86 mmol, CAS RN 289039-85-6) and sodium methanesulfinate (13.77 g, 134.9 mmol, CAS RN 20277-69-4) were added to the reaction mixture and the reaction mixture was heated at 120° C. for 2 h. The reaction mixture was allowed to cool down, poured on saturated aqueous sodium bicarbonate solution (500 mL) and ethyl acetate (500 mL) and filtered through celite. The organic layer was separated and the aqueous layer was extracted twice with ethyl acetate (200 mL each). The combined organic layers were washed with cold water (200 mL) and brine (100 mL), dried over anhydrous sodium sulfate and evaporated. The residue was purified by column chromatography over silica gel (100-200 mesh) with a gradient of ethyl acetate:n-hexane (1:10 to 2:10) to get the desired compound as a colorless solid (2.31 g, 55%). MS (EI): m/z=248 ([M]).

Example 17

4-{3-[Methyl-(5-o-tolyl-pyridazin-4-yl)-carbamoyl]-5-trifluoromethyl-benzenesulfonyl}-butyric acid tert-butyl ester

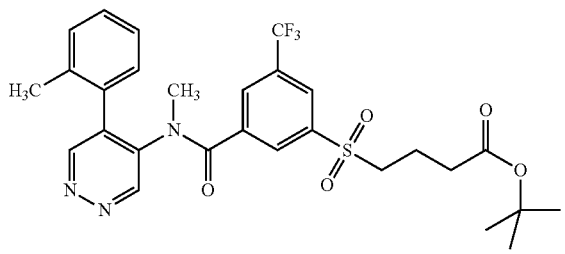 [SMILES: Cc1ccccc1-c1cnncc1N(C)C(=O)c1cc(C(F)(F)F)cc(S(=O)(=O)CCCC(=O)OC(C)(C)C)c1]

The title compound was prepared in analogy to example 1, from methyl-(5-o-tolyl-pyridazin-4-yl)-amine (example 11, intermediate a) and 3-(3-tert-butoxycarbonyl-propane-1-sulfonyl)-5-trifluoromethyl-benzoic acid (example 9, intermediate b). Light yellow foam (46%). MS (ESI⁺): m/z=578.19 ([M+H]⁺).

Example 18

4-{3-[Methyl-(5-o-tolyl-pyridazin-4-yl)-carbamoyl]-5-trifluoromethyl-benzenesulfonyl}-butyric acid

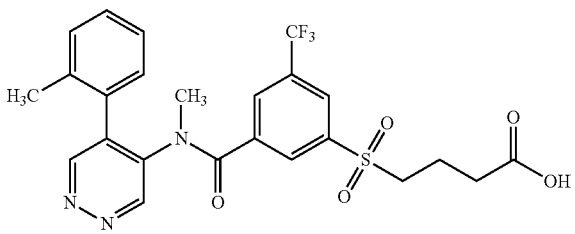 [SMILES: Cc1ccccc1-c1cnncc1N(C)C(=O)c1cc(C(F)(F)F)cc(S(=O)(=O)CCCC(=O)O)c1]

The title compound was prepared in analogy to example 10, from 4-{3-[methyl-(5-o-tolyl-pyridazin-4-yl)-carbamoyl]-5-trifluoromethyl-benzenesulfonyl}-butyric acid tert-butyl ester (example 16), adding another batch of trifluoroacetic acid after 3 hours (395 mg, 267 µL, 3.46 mmol) and stirring at room temperature for additional 64 hours. The product was further purified by a second chromatography using an MPLC (Flashmaster) system eluting with a gradient of CH₂Cl₂:methanol (100:0 to 90:10). Colorless oil (57%). MS (ESI⁺): m/z=522.13 ([M+H]⁺).

Example 19

N-Methyl-N-(4-o-tolyl-pyrimidin-5-yl)-3,5-bis-trifluoromethyl-benzamide

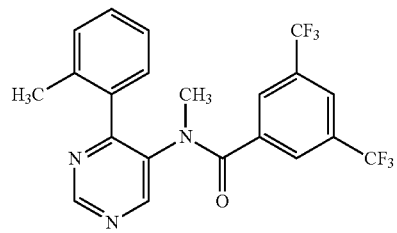 [SMILES: Cc1ccccc1-c1ncncc1N(C)C(=O)c1cc(C(F)(F)F)cc(C(F)(F)F)c1]

Methyl-(4-o-tolyl-pyrimidin-5-yl)-carbamic acid tert-butyl ester (120 mg, 0.40 mmol) was treated with 4M HCl in dioxane (3 mL) for 45 minutes after which all volatiles were removed under reduced pressure to give methyl-(4-o-tolyl-pyrimidin-5-yl)-amine as waxy oil. This material was dissolved in dichloromethane (3 mL) and treated with N-ethyl-diisopropyl-amine (210 µL, 1.2 mmol) and 3,5-bis-trifluoromethylbenzoyl chloride (166 mg, 0.60 mmol CAS RN 1271-19-8). After stirring for 1 h, the reaction mixture was loaded directly onto a silica gel column. Elution with 50% ethyl acetate in n-hexane yielded the desired compound as a yellow solid (78 mg, 44%). MS (ESI): m/z=440.1 [M+H]⁺.

Intermediates a) Methyl-(4-o-tolyl-pyrimidin-5-yl)-carbamic acid tert-butyl ester Sodium hydride (75 mg, 1.87 mmol) was added to a stirring solution of (4-o-tolyl-pyrimidin-5-yl)-carbamic acid tert-butyl ester (410 mmol, 1.44 mmol) in tetrahydrofuran (10 mL) under Argon atmosphere. After 10 min., iodomethane (117 μL, 1.87 mmol) was added. The reaction mixture was stirred for 16 hours and then poured into saturated aqueous sodium bicarbonate solution and extracted three times with ethyl acetate. The combined organic layers were washed with brine and dried over magnesium sulfate. Filtration followed by removal of volatiles gave the crude product. Flash chromatography on silica gel (33% ethyl acetate in n-hexane) gave the product as a yellow solid (242 mg, 56%) which was pure enough for the next step.

b) (4-o-Tolyl-pyrimidin-5-yl)-carbamic acid tert-butyl ester

4-Dimethylaminopyridine (109 mg, 0.9 mmol) was added to a solution of 4-o-tolyl-pyrimidin-5-ylamine (330 mg, 1.78 mmol) and di-tert-butyldicarbonate (389 mg, 1.78 mmol) in dichloromethane (10 mL). After stirring for 2 hours, the product was isolated in pure form by directly loading the reaction mixture onto a silica gel column and eluting with 25% ethyl acetate in n-hexane (420 mg, 83%).

c) 4-o-Tolyl-pyrimidin-5-ylamine

4-Chloro-5-nitro-6-o-tolyl-pyrimidine (580 mg, 0.23 mmol) and 10% palladium on carbon (125 mg, 0.116 mmol) in ethanol were stirred under 1 atmosphere of hydrogen pressure for 16 hours. Filtration followed by removal of volatiles gave the desired compound as a yellow solid (335 mg, 78%) which was used in the next step without further purification.

d) 4-Chloro-5-nitro-6-o-tolyl-pyrimidine

A stirring solution of 4,6-dichloro-5-nitropyrimidine (1.5 g, 7.73 mmol, CAS RN 4316-93-2), 2-methylphenyl boronic acid (1.16 g, 8.5 mmol), potassium carbonate (3.2 g, 23.2 mmol) and tetrakis-triphenylphosphine palladium(0) (447 mg, 0.30 mmol) in dioxane (50 mL) was heated under Argon atmosphere to 80° C. After 3 hours, the reaction mixture was cooled to room temperature and poured into saturated aqueous sodium bicarbonate solution and extracted three times with EtOAc. The combined organic layers were washed with brine and dried over MgSO$_4$. Filtration followed by removal of volatiles gave a brown solid. Column chromatography on silica gel (50-75% ethyl acetate in n-hexane) provided the title compound gave 4-chloro-5-nitro-6-o-tolylpyrimidine (621 mg, 32%).

The invention claimed is:
1. A compound of the formula

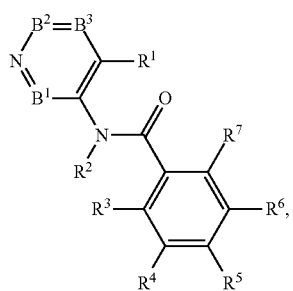

I wherein
$B^1$ is N and $B^2$ is $CR^9$ and $B^3$ is $CR^{10}$, or
$B^1$ is $CR^8$ and $B^2$ is N and $B^3$ is $CR^{10}$, or
$B^1$ is $CR^8$ and $B^2$ is $CR^9$ and $B^3$ is N;
$R^1$ is selected from the group consisting of
  phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkoxy, hydroxy-$C_{1-7}$-alkyl, hydroxy-$C_{1-7}$-alkoxy, $C_{1-7}$-alkoxy-$C_{1-7}$-alkyl, amino, $C_{1-7}$-alkylamino, di-$C_{1-7}$-alkylamino and phenyl-$C_{1-7}$-alkoxy, and
  heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy,
$R^2$ is selected from the group consisting of $C_{1-7}$-alkyl, halogen-$C_{1-7}$-alkyl, aminocarbonyl-$C_{1-7}$-alkyl and $C_{1-7}$-alkylsulfonyl-$C_{1-7}$-alkyl;
$R^3$ and $R^7$ are independently selected from the group consisting of hydrogen, halogen, $C_{1-7}$-alkyl and $C_{1-7}$-alkoxy;
$R^4$ and $R^6$ are independently from each other selected from the group consisting of hydrogen, $C_{1-7}$-alkyl, $C_{1-7}$-cycloalkyl, halogen, halogen-$C_{1-7}$-alkyl, halogen-$C_{1-7}$-alkoxy, hydroxy, hydroxy-$C_{1-7}$-alkyl, $C_{1-7}$-alkoxy, cyano, carboxyl, $C_{1-7}$-alkoxycarbonyl, $C_{1-7}$-alkoxycarbonyl-$C_{1-7}$-alkyl, $C_{1-7}$-alkylsulfonyl, hydroxy-$C_{1-7}$-alkylsulfonyl, $C_{1-7}$-alkoxy-$C_{1-7}$-alkylsulfonyl, carboxyl-$C_{1-7}$-alkylsulfonyl, $C_{1-7}$-alkoxycarbonyl-$C_{1-7}$-alkylsulfonyl, heterocyclylsulfonyl, aminosulfonyl, $C_{1-7}$-alkylaminosulfonyl, di-$C_{1-7}$-alkyl-aminosulfonyl, amino, $C_{1-7}$-alkylamino, di-$C_{1-7}$-alkylamino, nitro, unsubstituted heterocyclyl or heterocyclyl substituted with one or two groups selected from halogen, oxo and $C_{1-7}$-alkyl;
$R^5$ is selected from the group consisting of hydrogen, $C_{1-7}$-alkyl, halogen, halogen-$C_{1-7}$-alkyl and $C_{1-7}$-alkoxy; and
$R^8$, $R^9$ and $R^{10}$ are independently selected from the group consisting of hydrogen, $C_{1-7}$-alkyl, halogen and halogen-$C_{1-7}$-alkyl;
or pharmaceutically acceptable salts thereof.

2. A compound of formula I according to claim 1, wherein $B^1$ is N, $B^2$ is $CR^9$ and $B^3$ is $CR^{10}$.

3. A compound of formula I according to claim 1, wherein $B^1$ is $CR^8$, $B^2$ is N and $B^3$ is $CR^{10}$.

4. A compound of formula I according to claim 1, wherein $B^1$ is $CR^8$, $B^2$ is $CR^9$ and $B^3$ is N.

5. A compound of formula I according to claim 1, wherein $R^1$ is phenyl, said phenyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy, cycloalkyl-$C_{1-7}$-alkoxy, cyano, cyano-$C_{1-7}$-alkoxy, hydroxy-$C_{1-7}$-alkyl, hydroxy-$C_{1-7}$-alkoxy, $C_{1-7}$-alkoxy-$C_{1-7}$-alkyl, amino, $C_{1-7}$-alkylamino, di-$C_{1-7}$-alkylamino and phenyl-$C_{1-7}$-alkoxy.

6. A compound of formula I according to claim 1, wherein $R^1$ is phenyl, said phenyl being unsubstituted or substituted with one, two or three groups selected from the group consisting of $C_{1-7}$-alkyl, halogen and $C_{1-7}$-alkoxy.

7. A compound of formula I according to claim 1, wherein $R^1$ is heteroaryl, said heteroaryl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy.

8. A compound of formula I according to claim 1, wherein $R^1$ is pyridyl, said pyridyl being unsubstituted or substituted with one, two or three groups selected from the group consisting of $C_{1-7}$-alkyl, $C_{1-7}$-cycloalkyl, halogen, hydroxy, $C_{1-7}$-alkoxy, halogen-$C_{1-7}$-alkyl, halogen-$C_{1-7}$-alkoxy and cycloalkyl-$C_{1-7}$-alkoxy.

9. A compound of formula I according to claim 1, wherein $R^2$ is $C_{1-7}$-alkyl.

10. A compound of formula I according to claim 1, wherein $R^3$ and $R^7$ are hydrogen.

11. A compound of formula I according to claim 1, wherein $R^5$ is hydrogen.

12. A compound of formula I according to claim 1, wherein $R^4$ and $R^6$ are $R^4$ and $R^6$ are independently from each other selected from the group consisting of halogen-$C_{1-7}$-alkyl, $C_{1-7}$-alkylsulfonyl, carboxyl-$C_{1-7}$-alkylsulfonyl, $C_{1-7}$-alkoxycarbonyl-$C_{1-7}$-alkylsulfonyl and heterocyclylsulfonyl.

13. A compound of formula I according to claim 1, selected from the group consisting of
- N-[6-chloro-4-(4-fluoro-2-methoxy-phenyl)-pyridazin-3-yl]-3-methanesulfonyl-N-methyl-5-trifluoromethyl-benzamide,
- N-[4-(4-fluoro-2-methoxy-phenyl)-pyridazin-3-yl]-3-methanesulfonyl-N-methyl-5-trifluoromethyl-benzamide,
- N-[4-(4-fluoro-2-methoxy-phenyl)-6-methyl-pyridazin-3-yl]-3-methanesulfonyl-N-methyl-5-trifluoromethyl-benzamide,
- N-(6-chloro-4-o-tolyl-pyridazin-3-yl)-3-methanesulfonyl-N-methyl-5-trifluoromethyl-benzamide,
- N-(6-chloro-4-phenyl-pyridazin-3-yl)-3-methanesulfonyl-N-methyl-5-trifluoromethyl-benzamide,
- N-(6-chloro-4-phenyl-pyridazin-3-yl)-3-methanesulfonyl-N-methyl-5-trifluoromethyl-benzamide,
- N-(6-chloro-4-phenyl-pyridazin-3-yl)-N-methyl-3,5-bis-trifluoromethyl-benzamide
- N-[6-chloro-4-(2-methoxy-pyridin-3-yl)-pyridazin-3-yl]-3-methanesulfonyl-N-methyl-5-trifluoromethyl-benzamide,
- 4-{3-[(6-chloro-4-o-tolyl-pyridazin-3-yl)-methyl-carbamoyl]-5-trifluoromethyl-benzenesulfonyl}-butyric acid tert-butyl ester,
- 4-{3-[(6-chloro-4-o-tolyl-pyridazin-3-yl)-methyl-carbamoyl]-5-trifluoromethyl-benzenesulfonyl}-butyric acid,
- N-{6-chloro-4-[2-(2,2,2-trifluoro-ethoxy)-pyridin-3-yl]-pyridazin-3-yl}-3-methanesulfonyl-N-methyl-5-trifluoromethyl-benzamide,
- 3-methanesulfonyl-N-methyl-N-{4-[2-(2,2,2-trifluoro-ethoxy)-pyridin-3-yl]-pyridazin-3-yl}-5-trifluoromethyl-benzamide,
- 3-methanesulfonyl-N-methyl-N-{6-methyl-4-[2-(2,2,2-trifluoro-ethoxy)-pyridin-3-yl]-pyridazin-3-yl}-5-trifluoromethyl-benzamide,
- N-[5-(4-fluoro-2-methoxy-phenyl)-pyridazin-4-yl]-3-methanesulfonyl-N-methyl-5-trifluoromethyl-benzamide,
- 3-methanesulfonyl-N-methyl-N-(5-o-tolyl-pyridazin-4-yl)-5-trifluoromethyl-benzamide,
- 3-chloro-5-methanesulfonyl-N-methyl-N-(5-o-tolyl-pyridazin-4-yl)-benzamide,
- 4-{3-[methyl-(5-o-tolyl-pyridazin-4-yl)-carbamoyl]-5-trifluoromethyl-benzenesulfonyl}-butyric acid tert-butyl ester,
- 4-{3-[methyl-(5-o-tolyl-pyridazin-4-yl)-carbamoyl]-5-trifluoromethyl-benzenesulfonyl}-butyric acid,
- N-Methyl-N-(4-o-tolyl-pyrimidin-5-yl)-3,5-bis-trifluoromethyl-benzamide, and pharmaceutically acceptable salts thereof.

14. A compound of formula I according to any one of claim 1 for use as therapeutic active substance.

15. A pharmaceutical composition comprising a compound of formula I according to claim 1 and a pharmaceutically acceptable carrier and/or adjuvant.

* * * * *